United States Patent
Allen et al.

(10) Patent No.: US 9,655,982 B2
(45) Date of Patent: May 23, 2017

(54) FORMATION AND USES OF EUROPIUM COMPLEXES

(75) Inventors: Matthew J. Allen, Detroit, MI (US); Nipuni Dhanesha H. Gamage, Detroit, MI (US); Joel Garcia, Detroit, MI (US); Jeremiah Moore, Detroit, MI (US)

(73) Assignee: Wayne State University, Detroit, MI (US)

( * ) Notice: Subject to any disclaimer, the term of this patent is extended or adjusted under 35 U.S.C. 154(b) by 811 days.

(21) Appl. No.: 13/522,718

(22) PCT Filed: Jan. 19, 2011

(86) PCT No.: PCT/US2011/021643
§ 371 (c)(1),
(2), (4) Date: Dec. 12, 2012

(87) PCT Pub. No.: WO2011/090977
PCT Pub. Date: Jul. 28, 2011

(65) Prior Publication Data
US 2013/0078189 A1    Mar. 28, 2013

Related U.S. Application Data

(60) Provisional application No. 61/296,452, filed on Jan. 19, 2010, provisional application No. 61/408,111, filed on Oct. 29, 2010.

(51) Int. Cl.
*A61K 49/06* (2006.01)
*C09B 57/10* (2006.01)
*C09K 11/06* (2006.01)
*A61K 49/14* (2006.01)
*H01L 51/00* (2006.01)

(52) U.S. Cl.
CPC ............ *A61K 49/06* (2013.01); *A61K 49/14* (2013.01); *C09B 57/10* (2013.01); *C09K 11/06* (2013.01); *C09K 2211/182* (2013.01); *H01L 51/0089* (2013.01)

(58) Field of Classification Search
None
See application file for complete search history.

(56) References Cited

U.S. PATENT DOCUMENTS 4,777,023 A * 10/1988 Fieselmann ............ C01B 6/003
                                                                       136/258

OTHER PUBLICATIONS

Burai et al. EuII-cryptate with optimal water exchange and electronic relaxation: a synthon for potential pO2 responsive macromolecular MRI contrast agents. 2002 Chem. Commun. 20: 2366-2367.*
Higashiyama et al. Synthesis and fluorescence properties of divalent europium-poly(methacrylate containing [2.2.2] cryptand) complexes. 1993 Chem. Lett. : 1555-1558.*
Bilgin et al. Synthesis and characterization of novel metal-free phthalocyanines substituted with four diazadithiatetraoxa or diazahexaoxamacrobicyclic moieties. 2002 Tetrahedron Lett. 43: 5343-5347.*
Alston, D.R. et al., "Synthesis of an Octamethyl-18-Crown-6 Derivative and the X-Ray Crystal Structure of its 2:1 Complex With Borane-Ammonia," Tetrahedron v. 41, n. 14, 1985, pp. 2923-2926.
Still, W.C. et al., "Rapid Chromatographic Technique for Preparative Separations with Moderate Resolution," J. Org. Chem., v. 43, n. 14, 1978, pp. 2923-2925.
Gansow, O.A. et al., "Synthesis and Chemical Properties of Lanthanide Cryptates," J. Am. Chem. Soc. 1977, 99, pp. 7087-7089.
Nwe, K. et al., "PARACEST Properties of a Dinuclear Neodymium(III) Complex Bound to DNA or Carbonate," J. Bioconj. Chem. 2009, 20, pp. 1375-1382.
Viswanathan, S. et al., "Multi-Frequency PARACEST Agents Based on Europium(III)-DOTA-Tetraamide Ligands," Angew. Chem. Int. Ed. 2009, 48, pp. 9330-9333.
Suchy, M. et al., "Synthesis of MRI contrast agents derived from DOTAM-Gly-L-Phe-OH incorporating a disulfide bridge: Conjugation to a cell penetrating peptide and preparation of a dimeric agent," Bioorganic & Medicinal Chemistry Letters 20 (2010), pp. 5521-5526.
Woods, M. et al., "Europium(III) Macrocyclic Complexes with Alcohol Pendant Groups as Chemical Exchange Saturation Transfer Agents," J. Am. Chem. Soc. 2006, 128, pp. 10155-10162.
Adair, C. et al "Spectral properties of a bifunctional PARACEST europium chelate: an intermediate for targeted imaging applications," Contrast Media and Molecular Imaging 2007, 2, pp. 55-58.
Stadler, F. et al., "Crystal Structure, Physical Properties and HRTEM Investigation of the New Oxonitrodosilicate EuSi2O2N2," Chem. Eur. J. 2006, 12, pp. 6984-6990.
Denis, G. et al., "Structure and White Luminescence of Eu-Activated (Ba,Sr)13-xAl22-2xSi10+2xO66 Materials," Inorganic Chemistry, v. 47, n. 10, 2008, pp. 4226-4235.
Huxter, V.M. et al., "Demonstration of Bulk Semiconductor Optical Properties in Processable Ag2S and EuS Nanocrystalline Systems," Adv. Mater. 2008, 20, pp. 2439-2443.
Evans, W.J. et al., "Tethered Olefin Studies of Alkene versus Tetraphenylborate Coordination and Lanthanide Olefin Interactions in Metallocenes," J. Am. Chem. Soc. 2003, 125, pp. 5204-5212.
Datta, S. et al., "Aminotroponiminate Complexes of the Heavy Alkaline Earth and the Divalent Lanthanide Metals as Catalyst sfor the Hydroamination/Cyclization Reaction," Organometallics 2008, 27, pp. 1207-1213.
Edelmann, F.T., "Lanthanide amidinates and guanidinates: from laboratory curiosities to efficient homogenous catalyst and precursors for rare-earth oxide thin films," Chem. Soc.Rev. 2009, 38, pp. 2253-2268.

(Continued)

*Primary Examiner* — Michael G Hartley
*Assistant Examiner* — Jennifer Lamberski
(74) *Attorney, Agent, or Firm* — Brooks Kushman P.C.

(57) ABSTRACT

The present invention provides a method of forming an oxidatively-stable aqueous Eu(II) complex by synthesizing ligands that coordinate to large, soft, electron rich metals like Eu(II). The invention also provides an oxidatively stable aqueous Eu(II) complex. The complex can be used for a variety of purposes some of which include, but are not limited to, in paramagnetic chemical exchange saturation transfer, as a medical diagnostic, as a semiconductor, and for use in forming materials.

16 Claims, 15 Drawing Sheets

(56) References Cited

OTHER PUBLICATIONS

Richter, M.M. et al., "Electrogenerated Chemiluminescence. 58. Ligand-Sensitized Electrogenerated Chemiluminescence in Europium Labels," Analytical Chemistry, v. 68, n. 15, Aug. 1, 1996, pp. 2641-2650.
Su, F.H. et al, "New Observations on the Pressure Dependence of Luminescence from Eu2+-Doped MF2 (M=Ca, Sr, Ba) Fluorides," J. Phys. Chem. A 2008, 112, pp. 4772-4777.
Petrykin, V. et al., "Direct Synthesis of BaAl2S4:Eu2+ Blue Emission Phosphor by One-Step Sulfurization of Highly Homogenous Oxide Precursor Prepared via Solution-Based Method," Chem. Mater. 2008, 20, pp. 5128-5130.
Ahn, K. et al, "Preparation, heat capacity, magnetic properties, and the magnetocaloric effect of EuO," J. Appl. Phys. 2004, 97, pp. 1-5.
Hasegawa Y. et al., "Remarkable Magneto-Optical Properties of Europium Selenide Nanoparticles with Wide Energy Gaps," J. Am. Chem. Soc. 2008, 130, pp. 5710-5715.
Regulacio, M.D. et al., "Size-Dependent Magnetism of EuS Nanoparticles," Chem. Mater. 2008, 20, pp. 3368-3376.
Toth, E. et al., "Similarities and differences between the isoelectronic GdIII and EuII complexes with regard to MRI contrast agent applications," Coordination Chemistry Reviews 2001, 216-217, pp. 363-382.
Viswanathan, S. et al., "Alternatives to Gadolinium-Based Metal Chelates for Magnetic Resonance Imaging," Chem. Rev. 2010, 110, pp. 2960-3018.
Kauffmann, E. et al., "A Study of the Inclusive and Exclusive Cesium Cryptates in Nonaqueous Solvents by 133Cs NMR," J. Am. Chem. Soc. 1980, 102:7, pp. 2274-2278.
Burai, L. et al., "Novel Macrocyclic EuII Complexes: Fast Water Exchange Related to an Extreme M-Owater . Distance," Chem. Eur. J. 2003, 9, pp. 1394-1404.
Burai, L. et al., "EuII-cryptate with optimal water exchange and electronic relaxation: a synthon for potential pO2 responsive macromolecular MRI contrast agents," Chem. Commun. 2002, pp. 2366-2367.
Sabbatini, M. et al., "Photophysical Properties of Europium(II) Cryptates," J. Phys. Chem. 1984, 88, pp. 1534-1537.
Yuan, Jun-Lin et al., "Rietveld refinement and photoluminescent properties of a new blue-emitting material: Eu2+ activated SrZnP2O7," J. Solid State Chem. 2007, 180, pp. 3310-3316.
Evans, W.J. et al., "Synthesis, Structure, and Reactivity of Unsolvated Triple-Decked Bent Metallocenes of Divalent Europium and Yttterbium," Organometallics 1999, 18, pp. 1460-1464.
Hauber, Sven-Oliver et al., "Stabilization of Unsolvated Europium and Ytterbium Pentafluorophenyls by $_\pi$-Bonding Encapsulation through a Sterically Crowded Triazenido Ligand," Inorganic Chemistry, v. 44, n. 24, 2005, pp. 8644-8646.
Guo, H. et al., "Synthsis and structural characterization of novel mixed-valent samarium and divalent ytterbium and europium complexes supported by amine bis(phenolate) ligands," Dalton Trans., 2007, pp. 3555-3561.
Puchta, R. et al., "Host-Guest Complexes of Bicyclic Hexaamine Cryptands—Prediction of Ion Selectivity by Quantum Chemical Calculations. III," Aust. J. Chem. 2007, 60, pp. 889-897.
Dugah, D.T. et al., "Synthesis and characterization of new divalent lanthanide complexes supported by amine bis(phenolate) ligands and their applications in the ring opening polymerization of cyclic esters," Dalt Trans. 2008, pp. 1436-1445.
Cox, B.G. et al., "Kinetics and Equillbria of Alkaline-Earth-Metal Complex Formation with Cryptands in Methanol," J. Phys. Chem. 1984, 88, pp. 996-1001.
Dantz, D.A. et al., "Effects of the benzosubstitution of cryptands for the complex formation between protons, alkali and alkaline earth cations in water," Polyhedron 1998, 17, pp. 1891-1895.
Bemtgen, J.M. et al., "Formation and Dissociation Kinetics of Alkaline-Earth Ions with Benzo-Substituted Cryptands," Inorg. Chem. 1984, 23, pp. 3348-3353.
Gagne, R. et al., "Ferrocene as an Internal Standard for Electrochemical Measurements," Inorg. Chem. 1980, 19, pp. 2854-2855.
Denmark, S.E. et al., "Catalytic, Enantioselective, Vinylogous Aldol Reactions," Angew. Chem. Int. Ed. 2005, 44, pp. 4682-4698.
Schetter, B. et al., "Modern Aldol Methods for the Total Synthesis of Polyketides," Angew. Chem. Int. Ed. 2006, 45, pp. 7506-7525.
Fukui, H. et al, "Asymmetric Total Synthesis of Botcinins C, D, and F," Organic Letters 2008, v. 10, n. 14, pp. 3153-3156.
Chakraborty, T. K. et al., "Total Synthesis of Cruentaren B," J. Org. Chem. 2008, 73, pp. 3578-3581.
Sabitha, G. et al., "A Concise and Efficient Synthesis of (5R,7S)-Kurzilactone and Its (5S,7R)-Enantiomer by the Mukaiyama Aldol Reaction," J. S. Synthesis 2009, pp. 3301-3304.
Wang, L. et al., "Formal Total Synthesis of N-Methylmaysenine," Org. Lett. 2009, 11, pp. 1809-1812.
Kobayashi, S. et al., "Lanthanide Triflates as Water-Tolerant Lewis Acids. Activation of Commercial Formaldehyde Solution and Use in the Aldol Reaction of Silyl Enol Ethers with Aldehydes in Aqueous Media," J. Org. Chem. 1994, 59, pp. 3590-3596.
Kobayashi, S. et al., "Lanthanide Trifluoromethanesulfonate-Catalyzed Asymmetric Aldol Reactions in Aqueous Media," Org. Lett. 2001, 3, pp. 165-167.
Hamada, T. et al., "Catalytic Asymmetric Aldol Reactions in Aqueous Media Using Chiral Bis-pyridino-18-crown-6-Rare Earth Metal Triflate Complexes," J. Am. Chem. Soc. 2003, 125, pp. 2989-2996.
Dissanayake, P. et al., "Dynamic Measurements of Aqueous Lanthanide Triflate-Catalyzed Reactiolns Using Luminescence Decay," J. Am. Chem. Soc. 2009, 131, pp. 6342-6343.
Caravan, P. et al., Gadolinium(III) Chelates as MRI Contrast Agents: Structure, Dynamics, and Applications, Chem. Rev. 1999, 99, pp. 2293-2352.
Kobayashi, S. et al., "The Aldol Reaction of Silyl Enol Ethers with Aldehydes in Aqueous Media," Tetrahedron Lett. 1992, v. 33, n. 12, pp. 1625-1628.
Horrocks, W.D. Jr. et al., "Lanthanide Ion Probes of Structure in Biology. Laser-Indused Luminescence Decay Constants Provide a Direct Measure of the Number of Metal-Coordinated Water Molecules," J. Am. Chem. Soc. 1979, 101, pp. 334-340.
Corey, E.J. et al., "A Hypothesis for Conformational Restriction in Complexes of Formyl Compounds with Boron Lewis Acids. Experimental Evidence for Formyl CH—O and CH—F Hydrogen Bonds," Tetrahedron Lett. 1997, 38, pp. 33-36.
Ishihara, K. et al., "Scope and Limitations of Chiral B[3,5-Bis(trifluoromethyl)phenyl]oxazaboralidine Catalyst for Use in the Mukaiyama Aldol Reaction," J. Org. Chem. 2000, 65, pp. 9125-9128.
Corey, E.J. et al., "The formyl C—H—O hydrogen bond as a critical factor in enantioselective Lewis-acid catalyzed reactions of aldehydes," Chem. Commun., 2001, pp. 1321-1329.

* cited by examiner

FORMATION AND USES OF EUROPIUM COMPLEXES

CROSS-REFERENCE TO RELATED APPLICATIONS

This application is the U.S. national phase of PCT Appln. No. PCT/US11/021643 filed Jan. 19, 2011 which claims priority to U.S. Provisional Application No. 61/296,452 filed Jan. 19, 2010 and U.S. Provisional Application No. 61/408,111 filed Oct. 29, 2010, the disclosures of which are incorporated in their entireties by reference herein.

BACKGROUND OF THE INVENTION

1. Field of the Invention

Generally, the present invention relates to the field of europium compounds. More specifically, the present invention relates to a compound for uses of these compounds.

2. Description of the Related Art

Europium is a metal about as hard as lead and is quite ductile. It becomes a superconductor when it is simultaneously at both high pressure (80 GPa) and at low temperature (1.8 K). The occurrence of superconductivity is due to the applied pressure driving europium from a divalent (J=7/2) state into a trivalent (J=0) state. In the divalent state, the strong local magnetic moment is thought to play a role in suppressing the superconductivity and so through eliminating this local moment the opportunity for superconductivity arises.

Europium is a reactive rare earth element; it rapidly oxidizes in air (bulk oxidation of a centimeter-sized sample within several days) and resembles calcium in its reaction with water. Samples of the metal element in solid form, even when coated with a protective layer of mineral oil, are rarely shiny.

Divalent europium is a mild reducing agent, and under atmospheric conditions, it is the trivalent form that predominates. Under anaerobic, and particularly under geothermal conditions, the divalent form is sufficiently stable such that it tends to be incorporated into minerals of calcium and the other alkaline earths. This is the cause of the "negative europium anomaly" that depletes europium from being incorporated into the most usual light lanthanide minerals such as monazite, relative to the chondritic abundance. Bastnasite, another lanthanide mineral, tends to show less of a negative europium anomaly than monazite does, and hence is the major source of europium today. The accessible divalent state of europium has always made it one of the easiest lanthanides to extract and purify, even when present in low concentration, as it usually is.

The magnetic and optical properties of the divalent state of europium make this ion extremely attractive for use in materials, catalysis, luminescence, magnetic, and diagnostic-medical applications. A major hindrance to the use of Eu(II) in many of these applications is the extreme propensity of the ion to oxidize to Eu(III), especially in aqueous solution. Research efforts aimed at increasing the stability of aqueous Eu(II) have yielded moderate success: even the aqueous Eu(II) complex (4,7,13,16,21,24-hexaoxa-1,10-diazabicyclo[8.8.8]hexacosane europium(II), 1-Eu), previously reported to have the most positive oxidation potential, is not stable enough in aqueous solution for practical use.

It would therefore be useful to develop and generate Eu(II) complexes in aqueous solution.

SUMMARY OF THE INVENTION

According to the present invention there is provided the most oxidatively stable aqueous Eu(II) complexes known to date. The present invention provides a method of forming an oxidatively-stable aqueous Eu(II) complex by synthesizing ligands that coordinate to large, soft, electron rich metals like Eu(II). The invention also provides an oxidatively stable aqueous Eu(II) complex. The complex can be used for a variety of purposes some of which include, but are not limited to, in paramagnetic chemical exchange saturation transfer, as a medical diagnostic, as a semiconductor, and for use in forming materials.

BRIEF DESCRIPTION OF THE DRAWINGS

Other advantages of the present invention will be readily appreciated as the same becomes better understood by reference to the following detailed description when considered in connection with the accompanying drawings wherein.

DETAILED DESCRIPTION OF THE PREFERRED EMBODIMENTS

Figure 1:
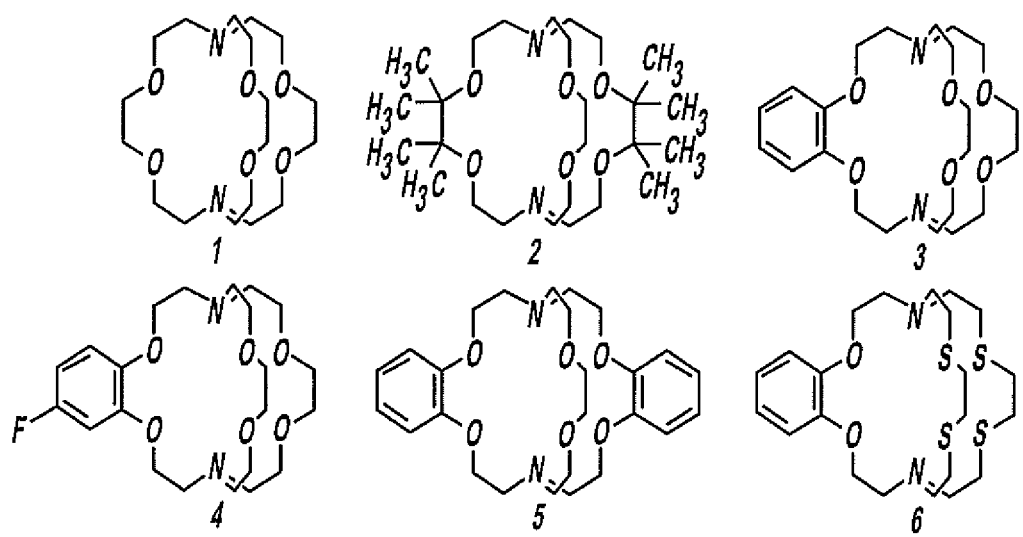
FIG. 1 shows ligands used to observe trends in oxidative stability of aqueous Eu(II) complexes.
Figure 2:
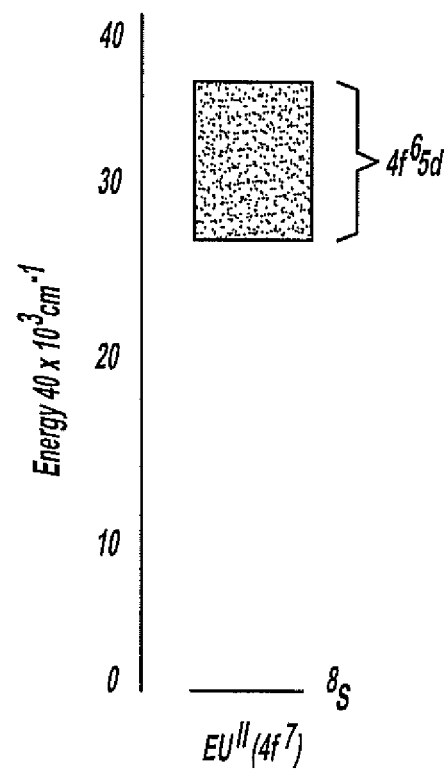
FIG. 2 shows the energy diagram that explains the luminescent characteristics (parity allowed 4f-5d transitions) of divalent Europium.
Figure 3:
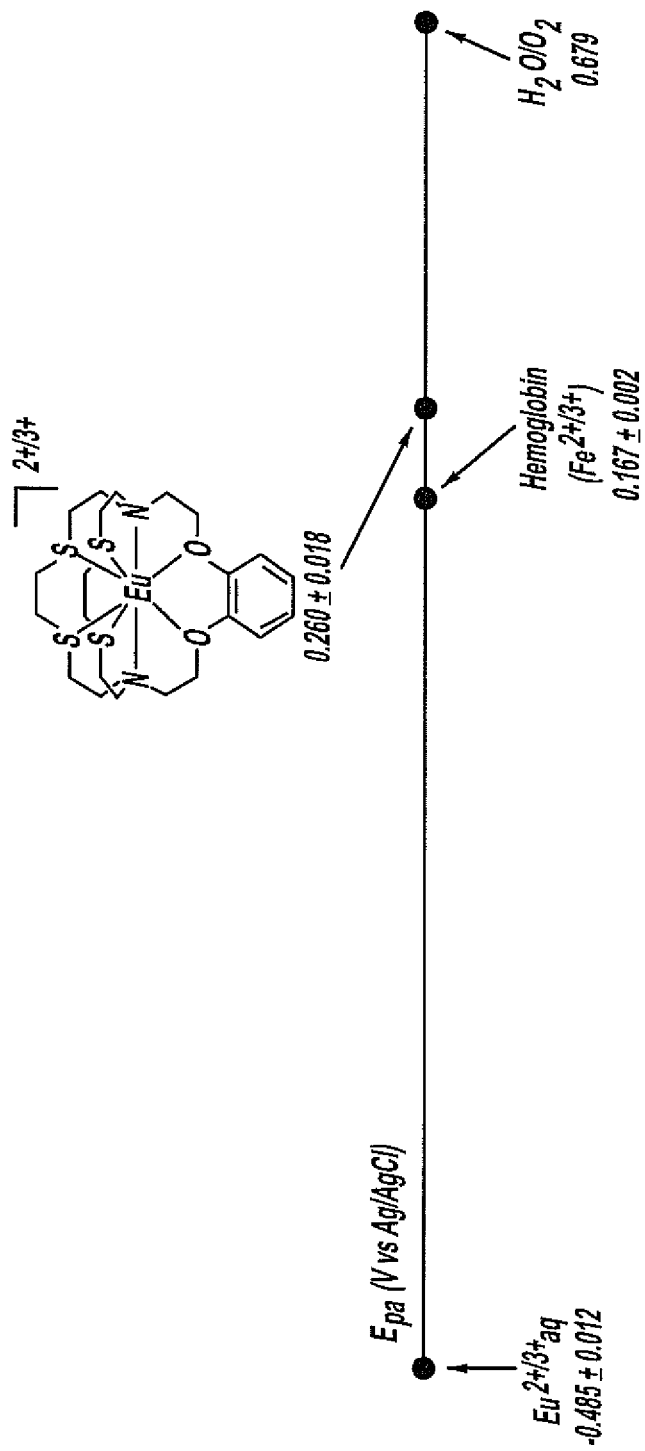
FIG. 3 shows the oxidative stabilization of Eu(II) using modified [2.2.2] cryptands leads to a more positive oxidation potential than Fe(II) in hemoglobin.
Figure 4:
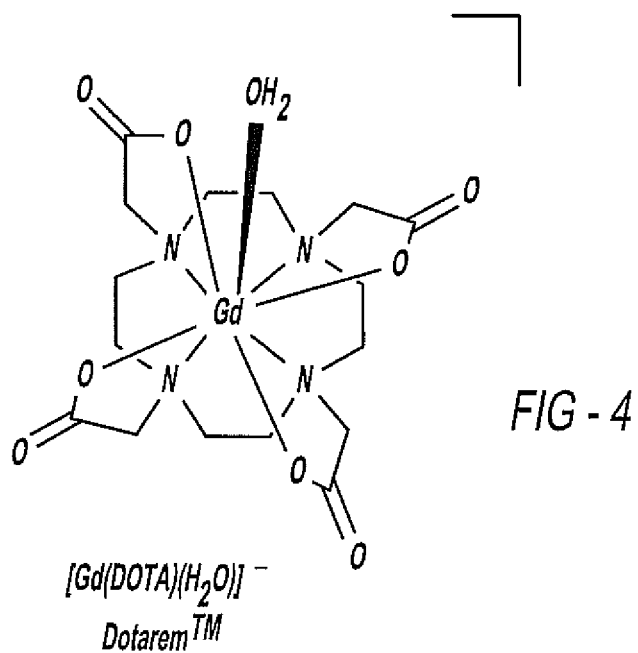
FIG. 4 shows an MRI contrast agent ([Gd(DOTA)(H$_2$O)]$^-$ that catalytically enhances the relaxation rate of water protons via magnetic dipolar interaction.
Figure 5:
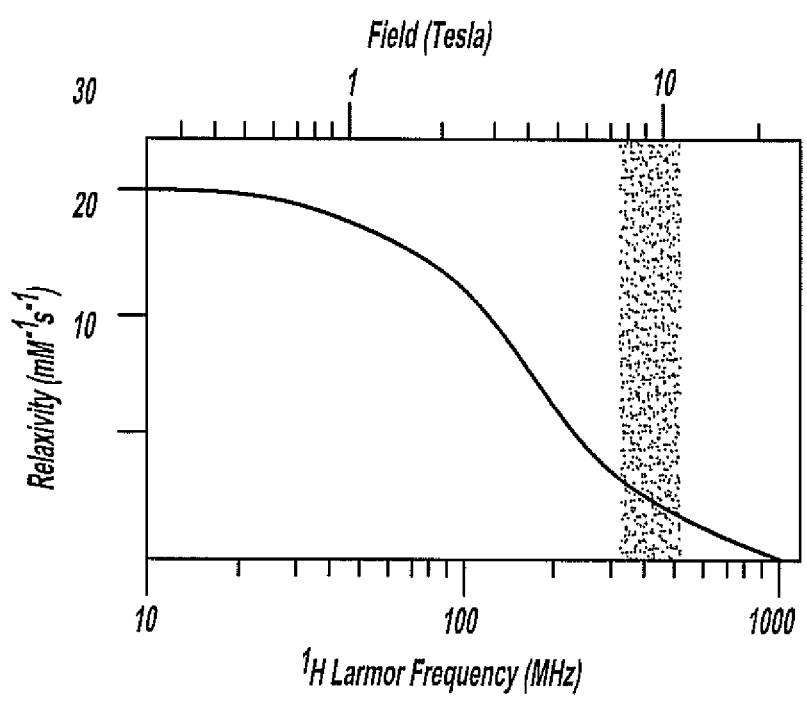
FIG. 5 shows the relaxivity profile of Gd(III)-based contrast agents at high field strengths, wherein relaxivity is the efficiency to enhance the relaxation rate of water protons.
Figure 6:
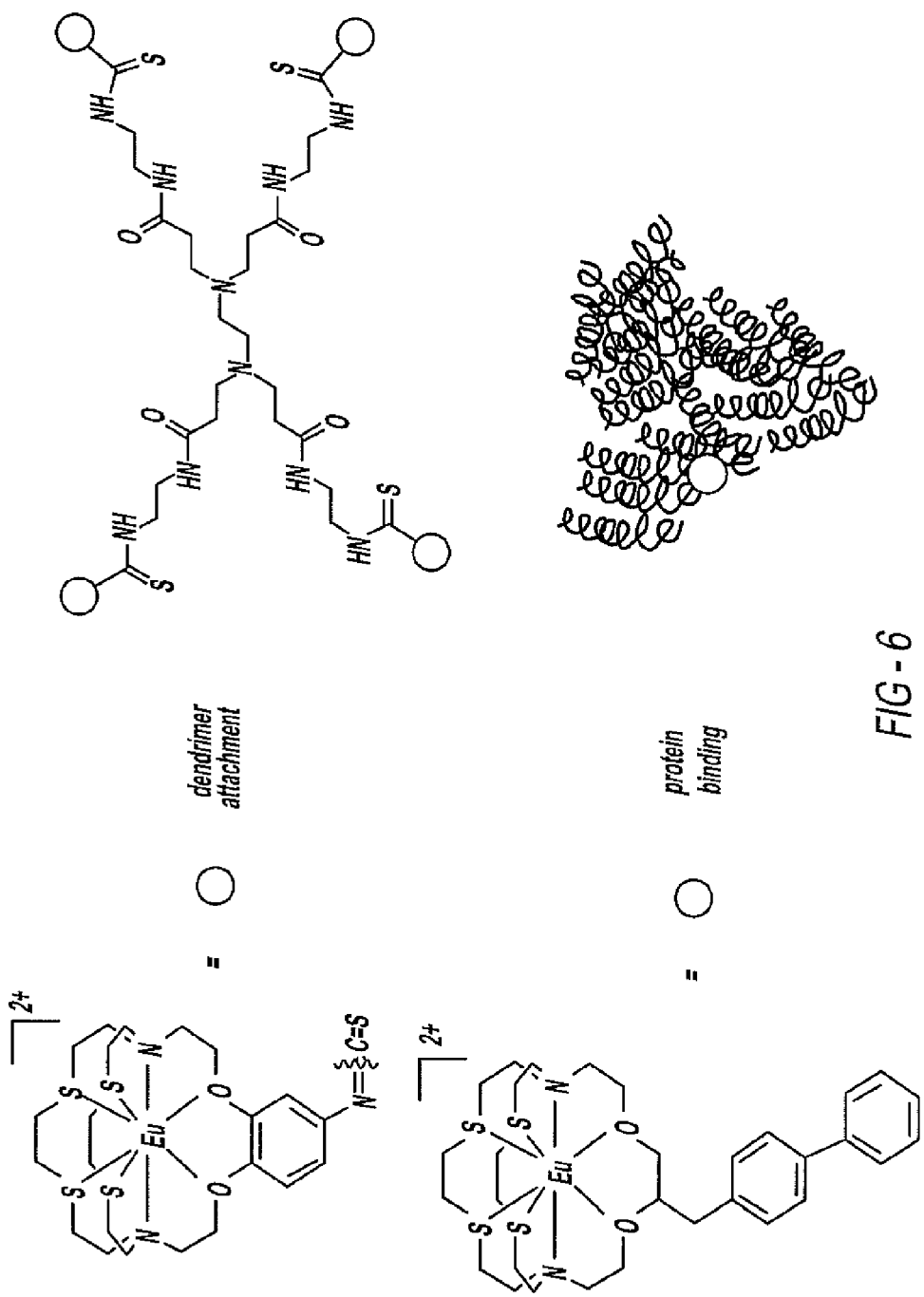
FIG. 6 shows mechanisms for reducing rotational correlation rate. The top method involves attachment to macromolecules including polymers or dendrimers, the bottom method represents interactions with biomolecules including proteins like human serum albumin.
Figure 7:
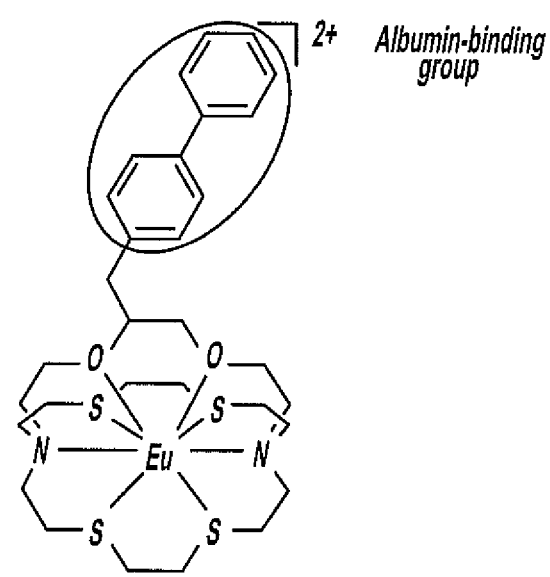
FIG. 7 shows how the biphenyl moiety of the complex of the present invention that exhibits high affinity to albumin.
Figure 8:
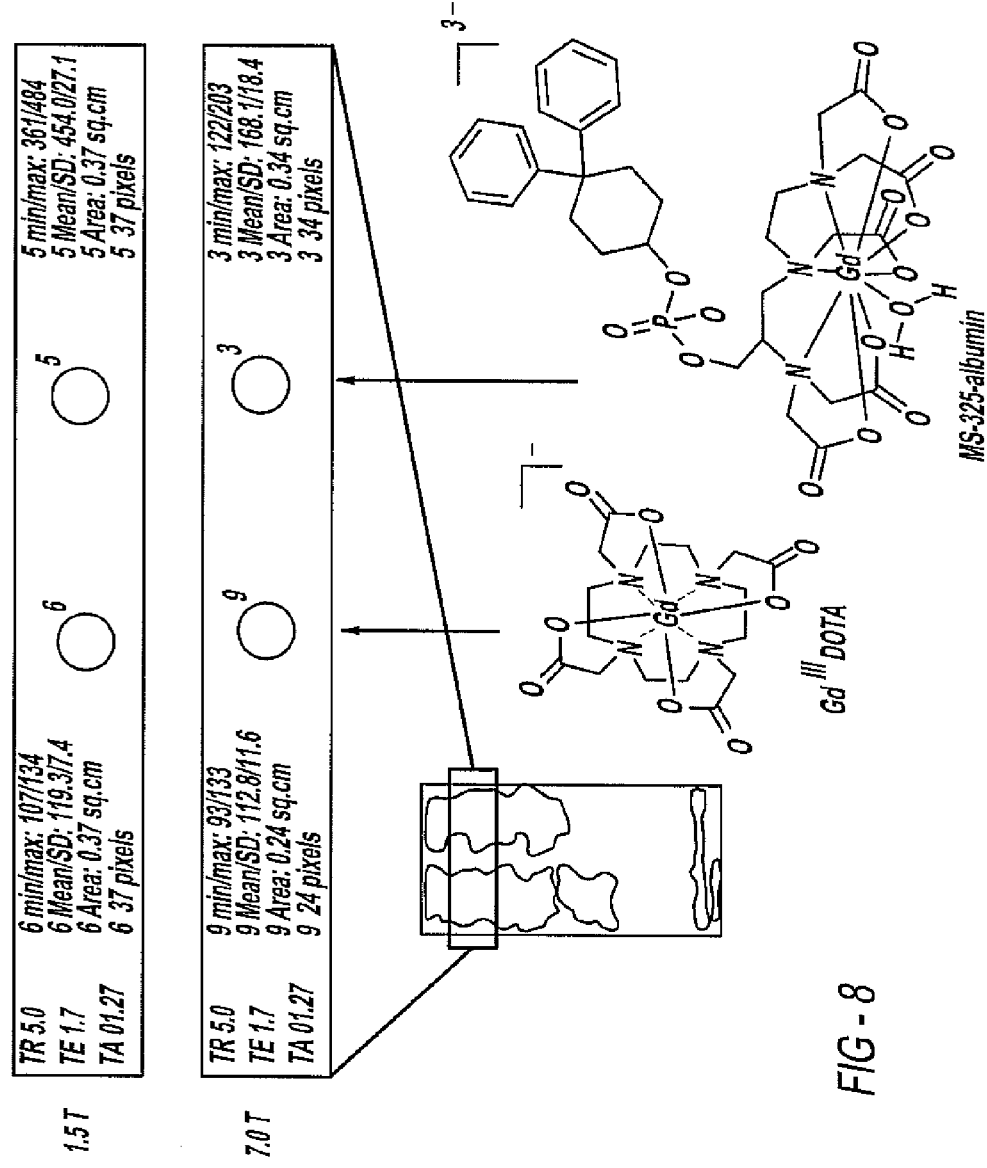
FIG. 8 shows how Gd(III)-based complexes, when bound to albumin give brighter images because of tumbling rate reduction.
Figure 9:
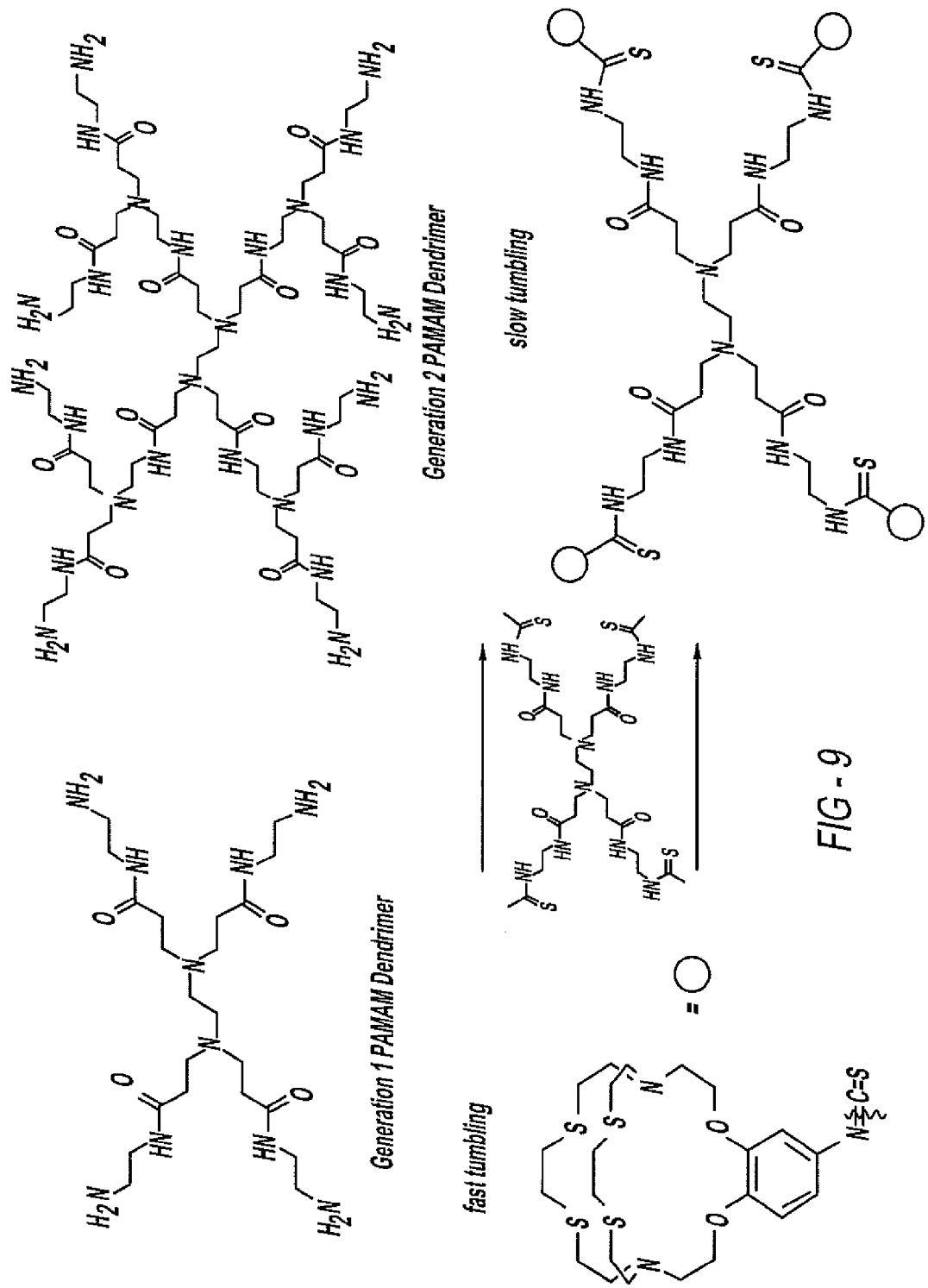
FIG. 9 shows how dendrimer attachment can be utilized.
Figure 10:
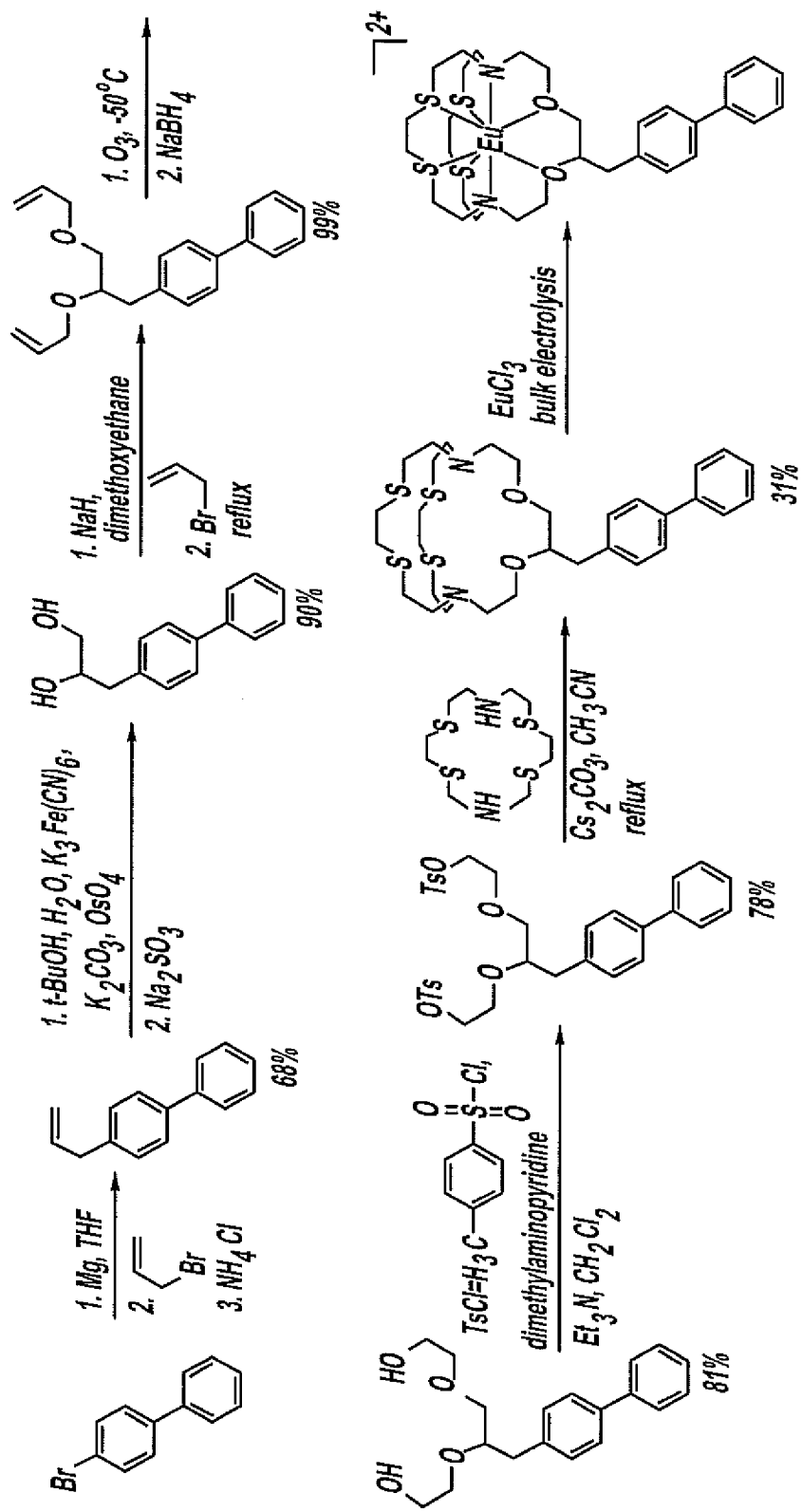
FIG. 10 shows the synthesis of tetrathiabiphenyl-based cryptate.
Figure 11:
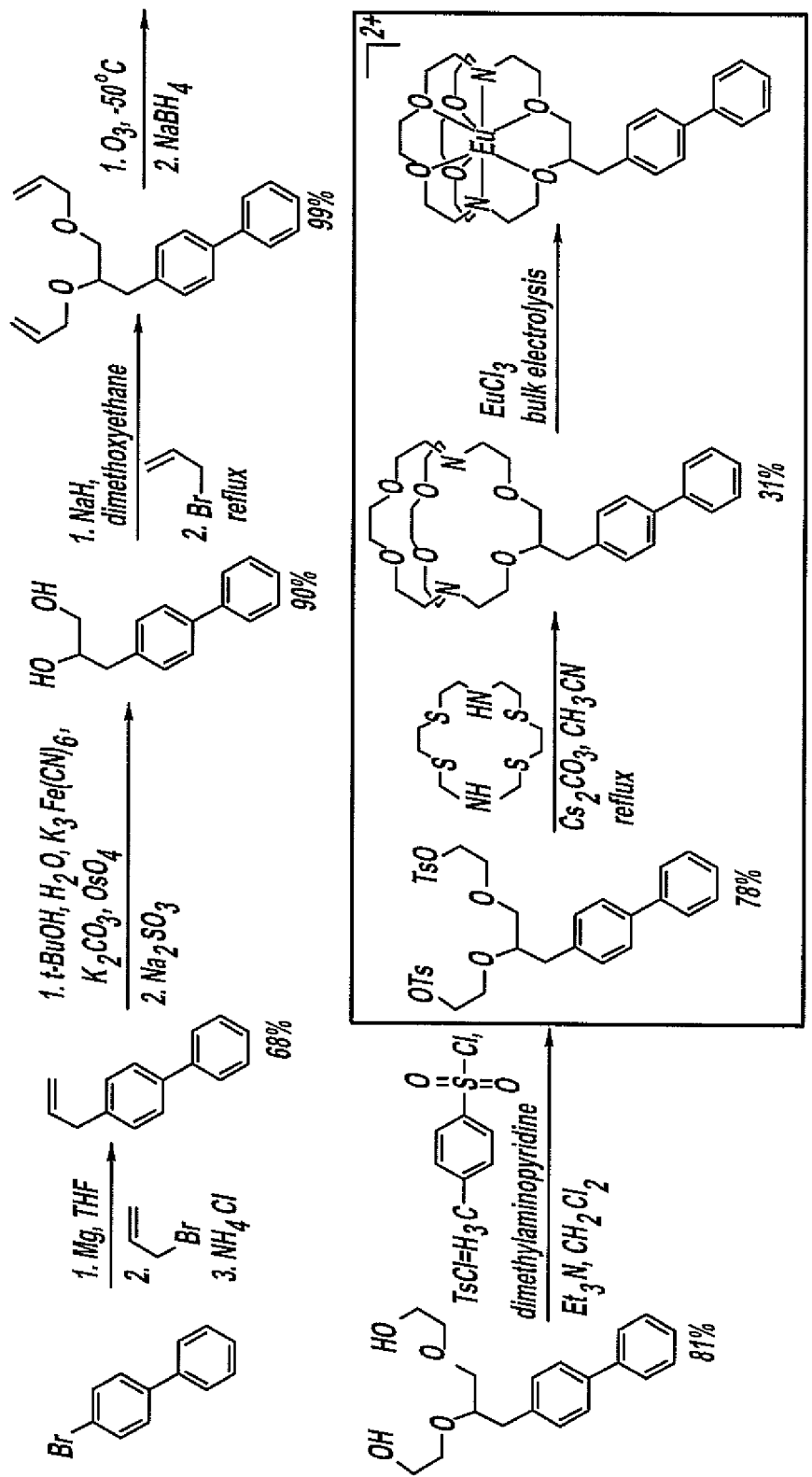
FIG. 11 shows the synthesis of the biphenyl-based cryptate.
Figure 12:
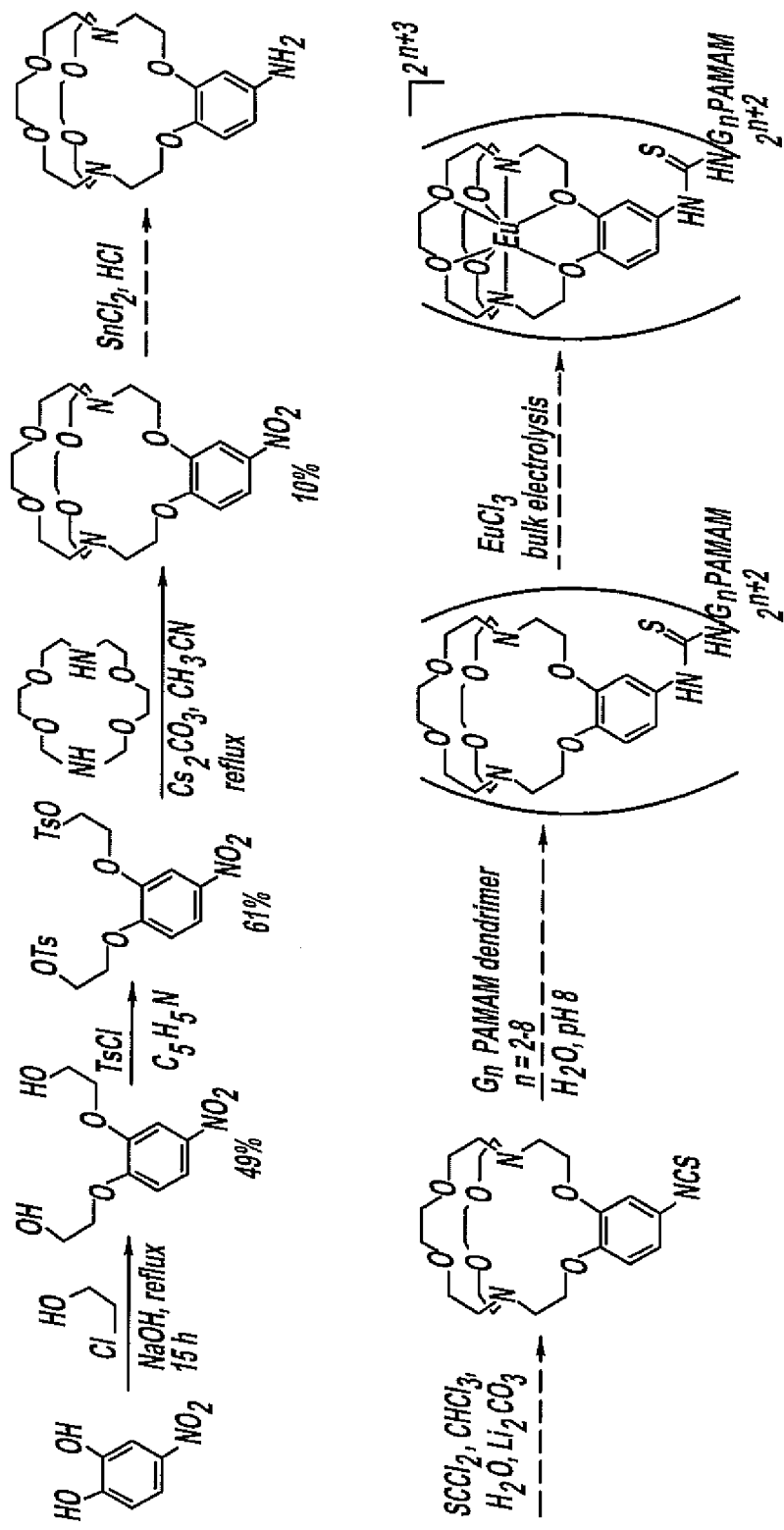
FIG. 12 shows the synthesis of the SCN-functionalized cryptate and attachment to dendrimers.
Figure 13:
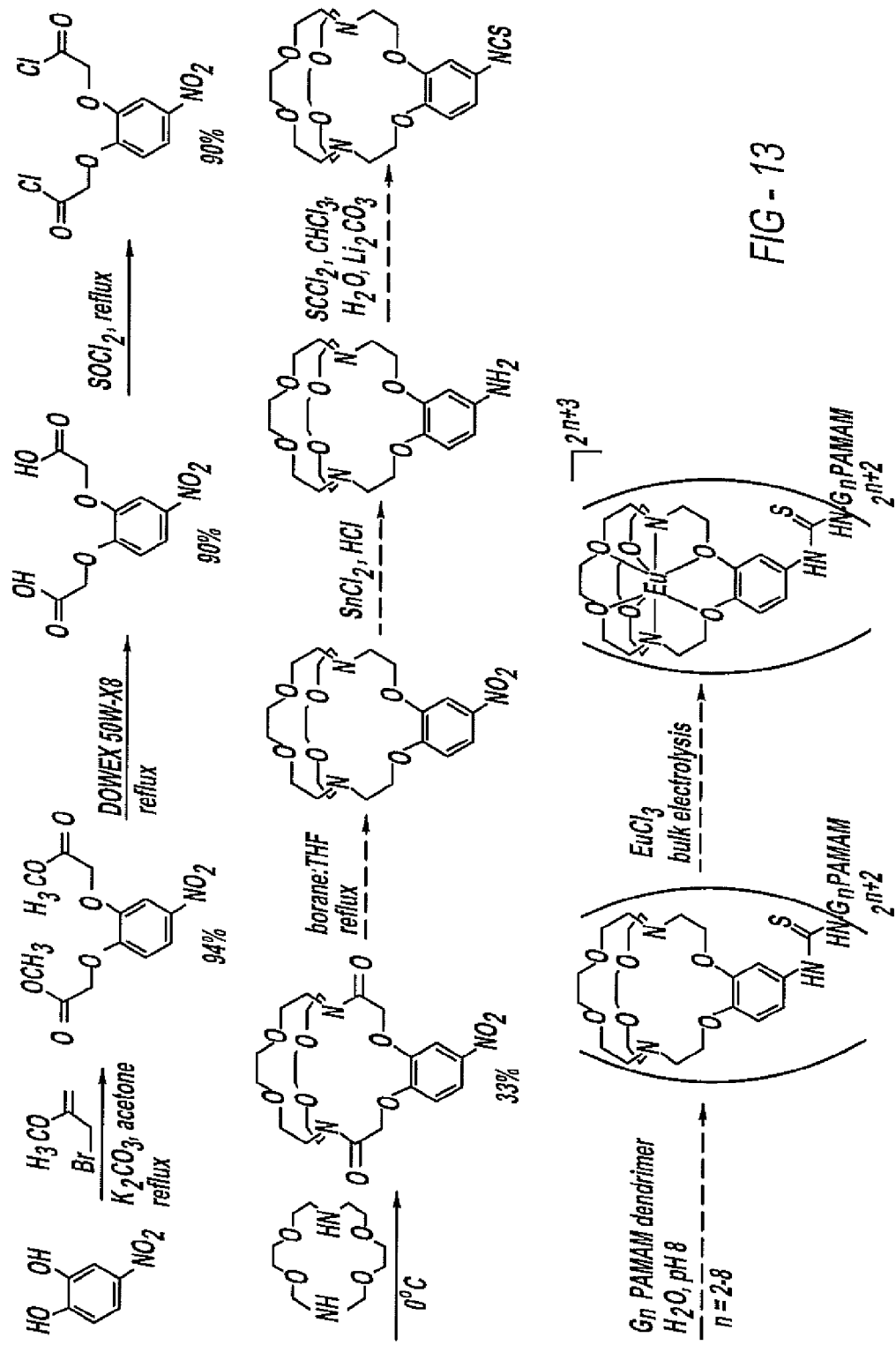
FIG. 13 shows an alternative synthesis of the SCN-functionalized cryptate with dendrimer attachment.
Figure 14:
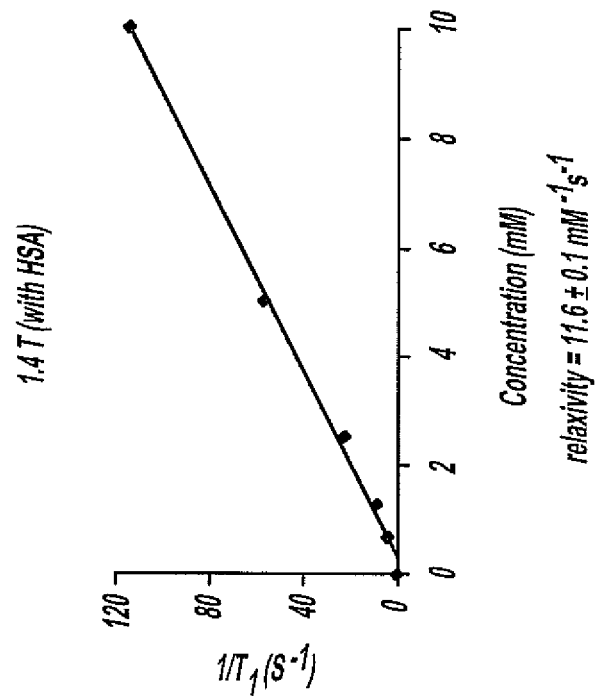
FIG. 14 shows that the addition of HSA to the biphenyl-based cryptate increases relaxivity.
Figure 14:
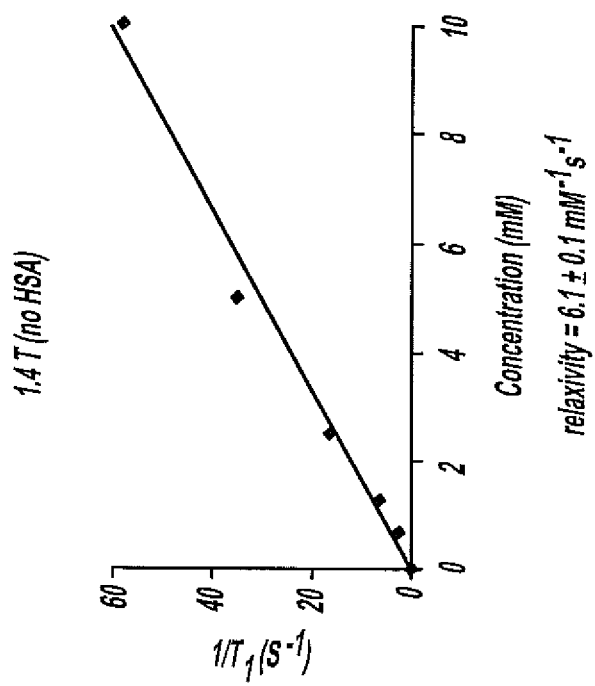
Figure 15:
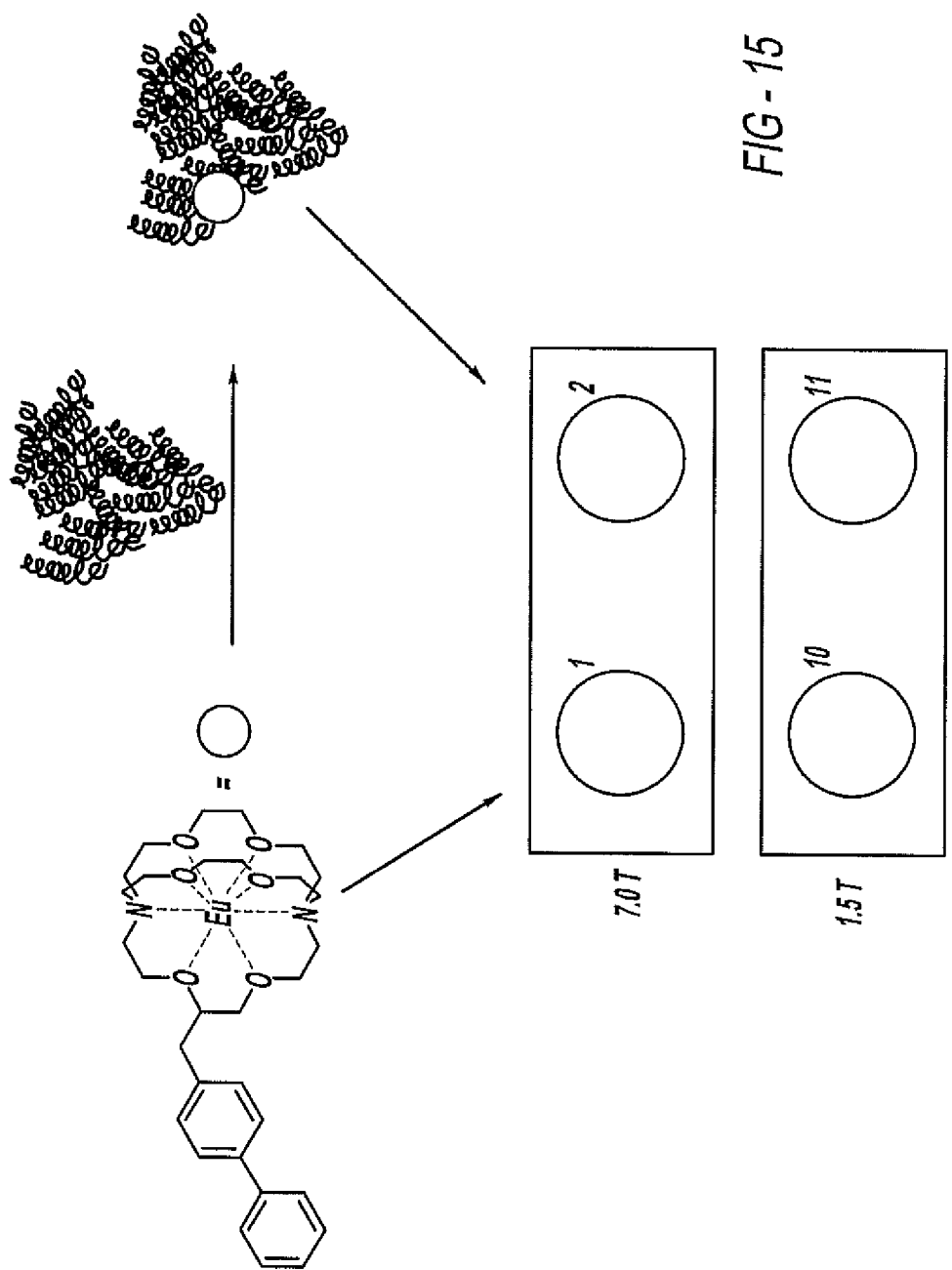
FIG. 15 shows that the addition of HSA to the biphenyl-based cryptate gives brighter images at 1.5 and 7 T.
Figure 16:
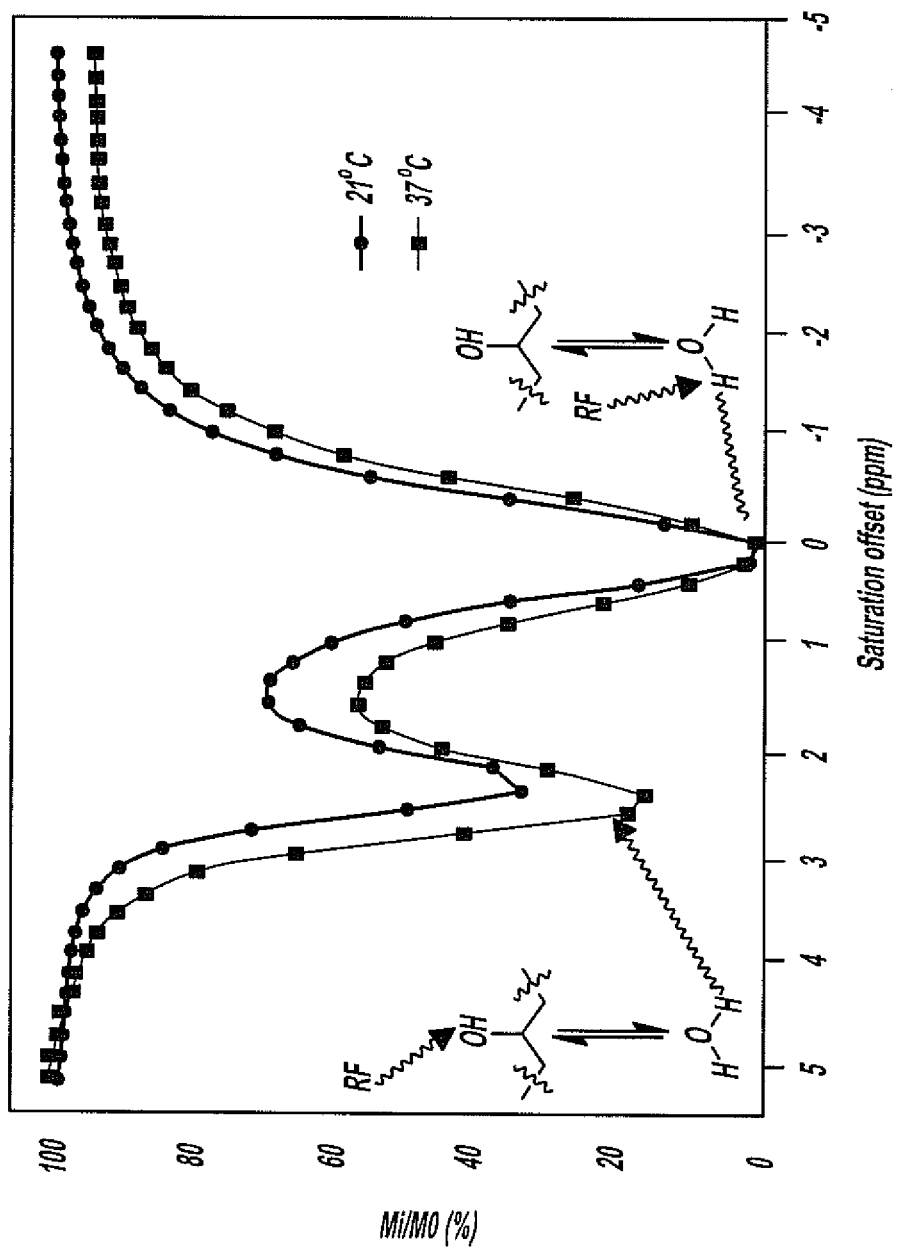
FIG. 16 shows the CEST spectrum of the europium(III) dimer.
Figure 17:
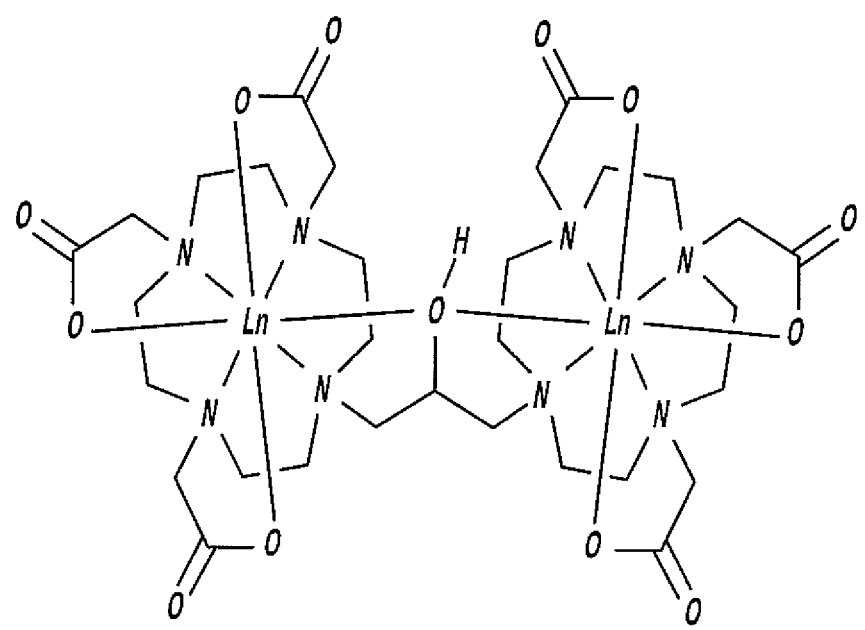
FIG. 17 shows the structure of the complex for use in PARACEST imaging, wherein Ln can be any lanthanide (III) ion.

Generally, the present invention provides a method for forming the most oxidatively stable aqueous Eu(II) complexes known to date. A strategy for favoring Eu(II) over Eu(III) in aqueous solution involves the synthesis and use of ligands that would preferentially coordinate to large, soft, electron rich metals like Eu(II). The template for the first ligand design was cryptand 1. This starting point was chosen because it previously was used to form the most oxidatively stable, aqueous Eu(II) complex. The stability of 1-Eu is partially due to the better size match of the cavity of cryptand 1 (1.4 Å) to the Eu(II) ion (1.25 Å) relative to the Eu(III) ion (1.07 Å).

Further oxidative stabilization can be achieved by modifying the structure of cryptand 1 using four principles of coordination chemistry to stabilize electron rich metals. Specifically, the goals are (1) to increase the steric bulk surrounding cryptand 1 to minimize Eu(II)—environment interactions; (2) to reduce the electron donating ability (Lewis basicity) of cryptand 1 to favor the electron rich Eu(II) over Eu(III); (3) to change the cavity size of the cryptand to better match the size of the Eu(II) ion; and (4) to modify the hard-soft acid-base properties of cryptand 1 to preferentially coordinate Eu(II) over Eu(III).

To implement these strategies, cryptands 1-6 (FIG. 1) were designed. To increase the steric bulk of 1, methyl groups were added to the methylene carbons between the oxygen atoms resulting in ligand 2. This methyl pattern was chosen because metal—environment interactions occur between the central methylene groups. Further, to examine the influence of Lewis basicity on oxidative stability, phenyl rings were introduced to decrease the electron-donating ability of the adjacent oxygen atoms of ligands 3-5 by a resonance withdrawing effect. The extent of electron withdrawal was modulated by varying the electron density of the phenyl ring through the addition of a fluorine atom (4) or by increasing the number of rings (5). Phenyl ring-containing cryptands 4-6 also have an influence on cavity size because each phenyl ring decreases the cavity size of the cryptand. The seemingly minor influence of the phenyl rings on cavity size was expected to have a noticeable effect on the oxidative stability of Eu(II) because of selectivity studies with group 2 cations using cryptands 1, 3, and 5. Finally, relatively soft S-atom donors were introduced in cryptand 6 in place of O-atom donors to explore the hard-soft acid-base preferences for the softer Eu(II) ion relative to the harder Eu(III) ion.

To synthesize the diverse set of cryptands 2 and 4-6, a three-step procedure was devised that involved common intermediates 7, 9, and 11 (Scheme 1). Briefly, the synthesis involved the conversion of the appropriate ethylenediols or catechols to the corresponding ditosylates (7, 9, and 11) followed by ring closure with 1,4,10,13-tetraoxa-7,16-diazacyclooctadecane, 2,2'-(ethylenedioxy)bis(ethylamine) or 1,4,10,13-tetrathia-7,16-diazacyclooctadecane. Metal complexation was achieved in situ by mixing Eu(NO$_3$)$_3$ and the desired cryptand (1-6), in aqueous solution and under an Ar atmosphere, while holding the potential at −0.8 V. Cyclic voltammograms were obtained for each complex in solution with ferrocene as an internal standard: a new anodic peak was observed for each complex at a more positive potential than the peak caused by the oxidation of the aqua ion (Table 1). These data indicate that each cryptand imparted additional stability to Eu(II) as designed.

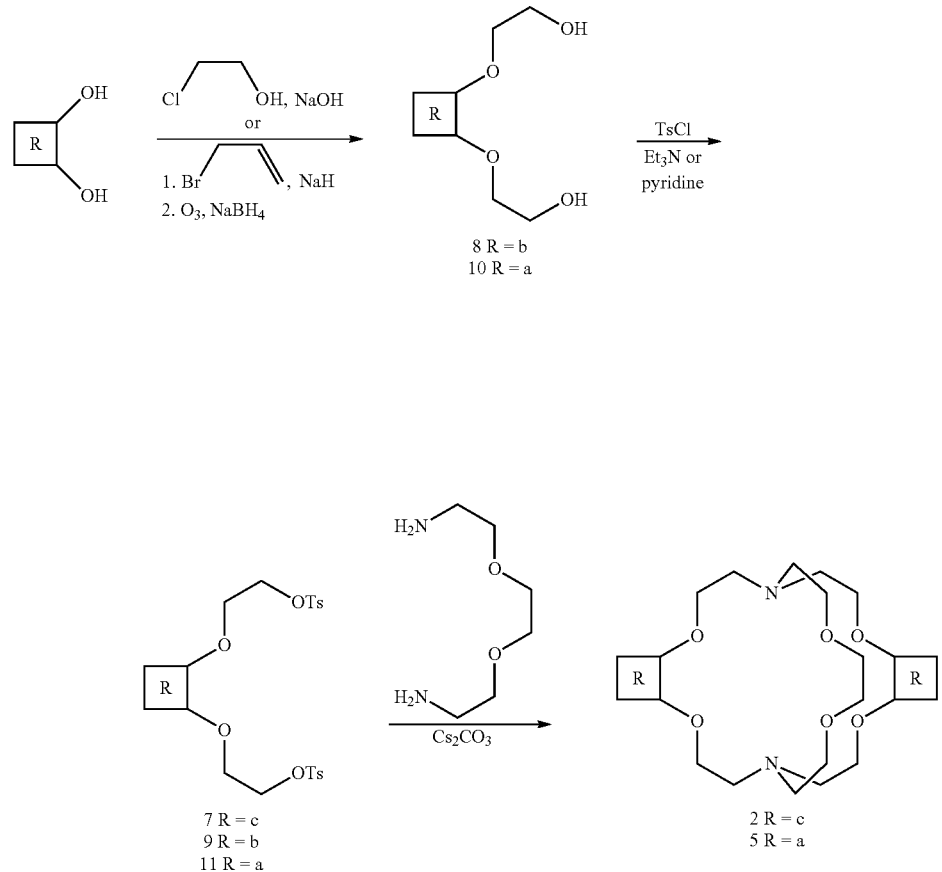

Scheme 1. Synthetic route to cryptands 2 and 4-6 using common intermediates 7, 9, and 11.

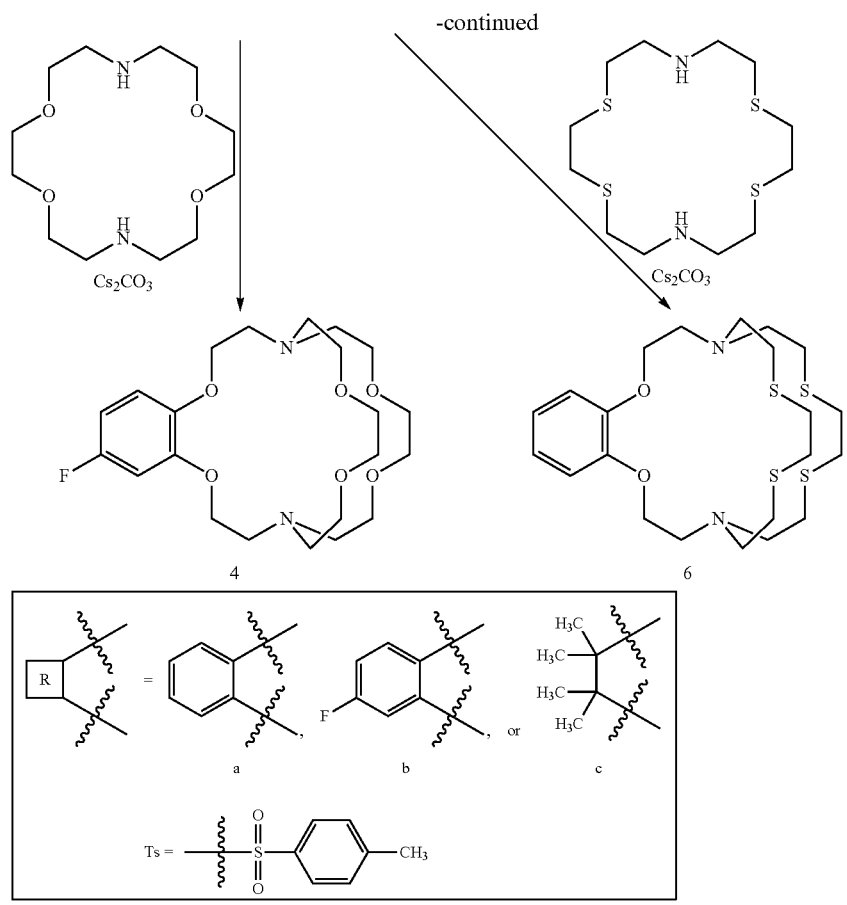

The cyclic voltammetric data of Eu-containing solutions of 1 and 2 demonstrate that the increased steric bulk in cryptand 2 leads to increased oxidative stability over unmodified cryptand 1. Additionally, the cryptands can contain either biphenyl or SCN groups.

TABLE 1

Anodic peak potentials (Epa) with respect to ferrocene/ferrocenium (Fc/Fc+). *

| Sample | $E_{pa}$ (V vs, Fc/Fc$^+$)[a] |
| --- | --- |
| 1 Eu(NO$_3$)$_3$ | −0.701 ± 0.030 |
| 2 1-Eu | −0.336 ± 0.016 |
| 3 5-Eu | −0.211 ± 0.004 |
| 4 3-Eu | −0.208 ± 0.009 |
| 5 2-Eu | −0.169 ± 0.006 |
| 6 4-Eu | −0.079 ± 0.007 |
| 7 hemoglobin | −0.070 ± 0.003 |
| 8 6-Eu | −0.035 ± 0.010 |

[a]Potentials are listed as mean ± standard error.

A more targeted examination of the influence of Lewis basicity on oxidative stability was achieved by examining the impact of ligands 3-5. It was observed that the use of one phenyl ring on cryptand 3 was sufficient to oxidatively stabilize Eu(II) by 128 mV (with respect to the unmodified cryptand 1-Eu). This increased stability is likely due to a combination of the drop in Lewis basicity of the adjacent oxygen atoms (better for electron rich metals) and the reduction in cavity size caused by the phenyl ring (better match for the size of the Eu(II) ion). However, the addition of a second phenyl ring (in cryptand 5) caused no significant difference in the anodic peak potential compared to the mono-phenyl substituted cryptand 3 (p=0.76). This counter-intuitive effect is likely due to reduction of the cavity size and not the decreased basicity of the ligand. In fact, the greater influence of cavity size on oxidative stability (versus Lewis basicity) is further supported by the influence of the addition of a fluorine substituent on the phenyl ring (cryptand 4). The oxidative stability attained with 4 is 133 mV greater than the stability obtained with the unsubstituted mono-phenyl cryptand 3. Additionally, the oxidative stability of 4-Eu is statistically identical to that of hemoglobin (p=0.64).

Finally, replacement of the harder oxygen atoms with softer sulfur atoms (cryptand 6) produced the most dramatic effect of the cryptand series. This modification increased the oxidative stability of Eu(II) by 173 mV compared to the structurally similar cryptand 3. The cavity size of cryptand 6 increases slightly due to the increased bond length of C—S compared to C—O, suggesting that a decrease in stability should be observed based on the difference between cryptands 1 and 3. But, the effect of cavity size is small relative to the influence of hard-soft acid-base matching of Eu(II) and sulfur. Cryptand 6 with Eu(II) is capable of producing an oxidative potential that is 666 mV more positive than the Eu aqua ion and 35 mV more positive than hemoglobin (Fe$^{2+/3+}$). This oxidative stability of Eu(II) is the highest reported in aqueous solution and indicates the potential for the use of Eu(II) in vivo.

Highly oxidatively stable Eu(II) complexes were obtained using modified cryptands. The trends in stability that were observed show ways to further stabilize aqueous Eu(II) and other lanthanide ions in the future. Finally, the most oxidatively stable complex, with an oxidation potential that indicates biological oxidative stability, opens the door for the use of the magnetic and optical properties of Eu(II) in vivo.

The present invention provides a dinuclear europium complex that exhibits highly favorable paramagnetic chemical exchange saturation transfer (PARACEST) properties that make it potentially useful as a contrast agent for magnetic resonance imaging (MRI). PARACEST-based contrast agents offer a new method to generate MR images with anatomical and biochemical information. They will add to the benefits of MRI by addressing several limitations of current clinical contrast agents. In the future they will be an important and versatile tool assisting medical diagnoses.

Previously, there was only one other dinuclear lanthanide complex that has been characterized as a PARACEST agent. (Nwe, K.; Andolina, C.; Huang, C.; Morrow, J. Bioconj. Chem. 2009, 20, 1375-1382.) The complex disclosed herein exhibits a low saturation offset of 2.4 ppm compared to other lanthanide PARACEST agents including the aforementioned dinuclear complex. (Viswanathan, S.; Ratnakar, S. J.; Green, K. N.; Kovacs, Z.; De León-Rodriguez, L. M.; Sherry, A. D. Angew. Chem. Int. Ed. 2009, 48, 9330-9333; Suchy, M.; Li, A. X.; Bartha, R.; Hudson, R. H. E. Bioorg. Med. Chem. 2008, 16, 6156-6166; Woods, M.; Woessner, D. E.; Zhao, P.; Pasha, A.; Yang, M.; Huang, C.; Vasalitiy, O.; Morrow, J. R.; Sherry, A. D. J. Am. Chem. Soc. 2006, 128, 10155-10162; Adair, C.; Woods, M. A.; Zhao, P.; Pasha, A.; Winter, P. M.; Lanza, G. M.; Athey, P.; Sherry, A. D.; Kiefer, G. E. Contrast Media and Molecular Imaging 2007, 2, 55-58.) This is in line with published reports of hydroxyl-bearing Eu complexes undergoing prototropic exchange exhibiting a substantially lower shift than water-exchanging complexes. Published Eu-based PARACEST agents reduce the bulk water signal by up to 45% in water while others require less polar solvents to observe PARACEST effects. The present data shows that the present dinuclear Eu complex reduces the bulk water signal by 84% in pure water, the highest reduction known for a Eu complex. Additionally, the Eu complex of the present invention exhibits greater bulk water signal suppression at 37° C. than at 21° C., which is favorable for in vivo PARACEST imaging. Furthermore, the same ligand can be used with Ce, Pr, Nd, Sm, Gd, Tb, Dy, Ho, Er, Tm, and Yb in addition to Eu as described.

The compounds of the present invention can be used in a variety of ways. For example: $Eu^{II}$-doped materials can be used to form other material examples of which include, but are not limited to, flat panel displays and light-emitting diodes; the compounds can also be used as semiconductors some non-limiting examples includes, but are not limited to, $Eu^{II}$ chalcogenide nanoparticles for use as optical isolators and magneto-optical memory; and, as mentioned above, the compounds can be used for biomedical imaging including, but not limited to, MRI imaging. Also, the disclosed compounds have fast water exchange rates ($10^8$-$10^9$ s$^{-1}$), high magnetic moments (7.6-8.0$\mu_B$), and symmetric $^8$S ground state.

The Examples below are included to demonstrate preferred embodiments of the invention. It should be appreciated by those of skill in the art that the techniques disclosed in the Examples represent techniques and compositions discovered by the inventors to function well in the practice of embodiments disclosed herein, and thus can be considered to constitute preferred modes for its practice. However, those of skill in the art should, in light of the present disclosure, appreciate that many changes can be made in the specific embodiments which are disclosed and obtain a like or similar result without departing from the spirit and scope of embodiments disclosed herein.

EXAMPLES

Example 1

Provided herein are oxidatively stable $Eu^{II}$ complexes in aqueous solution. FIG. 1 shows ligands used to observe trends in oxidative stability of aqueous EuII.

To synthesize the diverse set of cryptands 1-6, a three-step procedure was devised that involved common intermediates 7, 9, and 11 (Scheme 1). Briefly, the synthesis involved the conversion of the appropriate ethylenediols or catechols to the corresponding ditosylates (7, 9, and 11) followed by ring closure with 1,4,10,13-tetraoxa-7,16-diazacyclooctadecane, 2,2'-(ethylenedioxy)bis(ethylamine), or 1,4,10,13-tetrathia-7,16-diazacyclooctadecane. Metal complexation was achieved in situ by mixing Eu(NO$_3$)$_3$.5H$_2$O and the desired cryptand (1-6) in aqueous solution under an Ar atmosphere. The resulting solution was placed in a standard three-electrode cell (glassy-carbon working electrode, Pt-wire auxiliary electrode, and Ag/AgCl (1.0 M KCl) reference electrode). The potential at the carbon electrode was held at −0.8 V (vs Ag/AgCl) while stirring to produce $Eu^{II}$ in situ for metalation. After, metalation, cyclic voltammograms were obtained for each complex in solution with ferrocene as an internal standard: a new anodic peak was observed for each complex at a more positive potential than the peak corresponding to oxidation of the $Eu^{II}$ aqua ion (Table 1). These data indicate that each cryptand imparted additional stability to $Eu^{II}$ as hypothesized.

The cyclic voltammetric data of Eu-containing solutions of 1 and 2 demonstrate that the increased steric bulk in cryptand 2 leads to increased oxidative stability over unmodified cryptand 1. Furthermore, a more targeted examination of the influence of Lewis basicity on oxidative stability was achieved by examining the impact of ligands 3-5. It was observed that the use of one phenyl ring on cryptand 3 was sufficient to stabilize $Eu^{II}$ oxidatively by 128 mV with respect to the unmodified cryptand 1-Eu. This stabilization is likely due to a combination of the decrease in Lewis basicity of the adjacent oxygen atoms (better for electron-rich metals) and the reduction in cavity size caused by the phenyl ring (better match for the size of the $Eu^{II}$ ion). However, the addition of a second phenyl ring (5) caused no difference in the anodic peak potential compared to the mono-phenyl substituted cryptand 3 (p=0.76). This effect likely is due to reduction of the cavity size counteracting the decreased basicity of the ligand, suggesting that a minimum cavity size for $Eu^{II}$ stabilization was achieved with cryptand 3. Further decrease in Lewis basicity through the addition of a fluorine substituent to the phenyl ring (4) led to 129 mV greater stability than what was observed with unsubstituted monophenyl cryptand 3. Additionally, the oxidative stability of 4-Eu is not different from that of $Fe^{II}$ in hemoglobin (p=0.45).

Finally, replacement of the harder oxygen atoms with softer sulfur atoms (6) produced the most dramatic stabilization effect of the cryptand series. This modification increased the oxidative stability of $Eu^{II}$ by 173 mV compared to the structurally similar cryptand 3. The cavity size of cryptand 6 increases slightly due to the increased bond length of C—S compared to C—O, suggesting that a decrease in stability can be observed based on the difference between cryptands 1 and 3. However, the effect of cavity size is small relative to the influence of hard-soft acid-base matching between $Eu^{II}$ and sulfur. Cryptand 6 with $Eu^{II}$ produces an oxidative potential that is 666 mV more positive than the Eu aqua ion and 35 mV more positive than Fe(II) in hemoglobin. This oxidative stability of $Eu^{II}$ is the highest reported in aqueous solution and indicates the potential for the use of $Eu^{II}$ in vivo.

Dramatic oxidative stabilization of $Eu^{II}$ using modified cryptands was observed. The trends in stability that were observed suggest that further stabilization of aqueous $Eu^{II}$ and other lanthanide ions is possible. Finally, the most stable complex, with an oxidation potential indicative of biological oxidative stability, opens the door for the use of the magnetic and spectroscopic properties of $Eu^{II}$ in vivo.

Example 2

Materials and Methods

Commercially available chemicals were of reagent-grade purity or better and were used without further purification unless otherwise noted. Human hemoglobin was obtained from RayBiotech Inc. (catalog number: MD-22009P). Water was purified using a PURELAB Ultra Mk2 water purification system (ELGA). Dichloromethane was purified using a solvent purification system (Vacuum Atmospheres Company). Triethylamine was distilled from $CaH_2$. 2,2'-(2,3-Dimethylbutane-2,3-diyl)bis(oxy)bis(ethane-2,1-diyl)bis(4-methylbenzenesulfonate) was synthesized using a previously published procedure.

Flash chromatography was performed using silica gel 60, 230-400 mesh (EMD Chemicals). Analytical thin-layer chromatography (TLC) was carried out on ASTM TLC plates precoated with silica gel 60 F254 (250 μm layer thickness). TLC visualization was accomplished using a UV lamp followed by charring with potassium permanganate stain (3 g $KMnO_4$, 20 g $K_2CO_3$, 5 mL 5% w/v aqueous NaOH, 300 mL $H_2O$).

$^1H$ NMR spectra were obtained using a Varian Unity 300 (300 MHz) spectrometer and a Mercury 400 (400 MHz) spectrometer, $^{13}C$ NMR spectra were obtained using a Varian Unity 300 (75 MHz) spectrometer and a Mercury 400 (101 MHz) spectrometer. $^{19}F$ NMR spectra were obtained using Varian Unity 300 (282 MHz) spectrometer. Chemical shifts are reported relative to residual solvent signals unless otherwise noted ($CDCl_3$: $^1H$: δ 7.27, $^{13}C$: δ 77.23; $CD_3OD$: $^1H$: δ 3.31, $^{13}C$: δ 49.00; $CFCl_3$ (internal standard): $^{19}F$ δ 0.00). NMR data are assumed to be first order, and the apparent multiplicity is reported as "s"=singlet, "d"=doublet, "dd"=doublet of doublets, "t"=triplet, "td"=triplet of doublets, "q"=quartet, "m"=multiplet, or "brs"=broad singlet. Italicized elements are those that are responsible for the shifts. High-resolution electrospray ionization mass spectra (HRESIMS) were obtained on an electrospray time-of-flight high-resolution Waters Micromass LCT Premier XE mass spectrometer. Cyclic voltammetric analyses were performed using a WaveNow USB potentiostat (Pine Research Instrumentation). A standard three-electrode cell was used with a glassy-carbon working electrode, a Pt-wire auxiliary electrode, and a Ag/AgCl reference electrode (1.0 M KCl). All electrochemical experiments were performed under an Ar atmosphere at ambient temperature with $Et_4NClO_4$ (0.05 M) as the supporting electrolyte, an aqueous solution of 3-(N-morpholino)propanesulfonic acid (MOPS, 0.01 M, pH 7.5) as the solvent, and the ferrocene/ferrocinium (Fc/Fc+) redox couple as an internal standard. From the initial potential of the analysis (−1.5 V), the voltage was ramped to 0.75 V and back to −1.5 V at a scan rate of 150 mV/s. Data points were collected every 3.35 ms, and the measurements were repeated 3-6 times each with independently prepared samples. After each measurement, ferrocene (6.7 mM in acetonitrile) was added to the sample (0.13 mM ferrocene after addition) and the measurement was repeated to enable referencing to Fc/Fc+.

Synthetic Procedures and Characterization 5,5,6,6,14,14,15,15-Octamethyl-4,7,13,16,21,24-hexaoxa-1,10-diazabicyclo[8.8.8]hexacosane (2): To a mixture of $Cs_2CO_3$ (0.866 g, 2.66 mmol, 6 equiv) in acetonitrile (60 mL) at reflux was added a solution of ditosylate 7 (0.467 g, 0.907 mmol, 2.05 equiv) and 2,2'-(ethylenedioxy)bis(ethylamine) (649 μL, 0.443 mmol, 1 equiv) in acetonitrile (120 mL) dropwise over 48 hours. Upon completion of the addition, the resulting reaction mixture was heated at reflux for 48 hours. Solvent was removed under reduced pressure, and purification was performed using silica gel chromatography (stepwise gradient of 50:1→10:1→8:1 dichloromethane/methanol) to yield 61 mg (28%) of 2 as a yellow oil. $^1H$ NMR (300 MHz, $CD_3OD$, δ): 1.23 and 1.25 (overlapping s, $CH_3$, 24H), 2.51-2.72 (m, $CH_2$, 12H), 3.42-3.82 (m, $CH_2$, 16H); $^{13}C$ NMR (75 MHz, $CDCl_3$, δ): 20.8 ($CH_3$), 53.3 ($CH_2$), 56.9 ($CH_2$), 59.3 ($CH_2$), 67.8 ($CH_2$), 68.7 ($CH_2$), 81.1; TLC: $R_f$=0.46 (8:1 dichloromethane/methanol); HRESIMS (m/z): $[M+H]^+$ calcd for $C_{26}H_{53}N_2O_6$, 489.3904; found, 489.3914.

2,2'-(4-Fluoro-1,2-phenylene)bisoxydiethanol (8): To a degassed solution of water (1 mL), 1-butanol (2.5 mL), and NaOH (0.545 g, 13.6 mmol, 3 equiv) under an atmosphere of Ar was added 4-fluorobenzene-1,2-diol (0.580 g, 4.54 mmol, 1 equiv), and the resulting mixture was heated at reflux. After 5 minutes at reflux, a solution of 2-chloroethanol (912 μL, 13.6 mmol, 3 equiv) in degassed 1-butanol (15 mL) was added dropwise over 1 hour while maintaining reflux. The resulting solution was heated at reflux for 18 hours at which point the solvent was removed under reduced pressure. Purification was performed using silica gel chromatography (stepwise gradient of 1:0→40:1→20:1→5:1 dichloromethane/methanol) to yield 643 mg (66%) of 8 as a pale brown solid. $^1H$ NMR (300 MHz, $CD_3OD$, δ): 3.82-3.93 (m, $CH_2$, 4H), 4.04 (q, J=4.8 Hz, $CH_2$, 4H), 6.60 (td, J=9.0, 3.3 Hz, CH, 1H), 6.79 (dd, J=3.0, 10.5 Hz, CH, 1H), 6.91-6.99 (m, CH, 1H); $^{13}C$ NMR (75 MHz, $CD_3OD$, δ): 61.5 ($CH_2$), 61.7 ($CH_2$), 72.0 ($CH_2$), 72.9 ($CH_2$), 103.1 (d, $^2J_{C-F}$=27.2 Hz, CH), 107.4 (d, $^2J_{C-F}$=22.1 Hz, CH), 116.68 (d, $^3J_{C-F}$=10.0 Hz, CH), 146.4 (d, $^4J_{C-F}$=2.3 Hz), 151.4 (d, $^3J_{C-F}$=10.1 Hz) 159.1 (d, $^1J_{C-F}$=237.7 Hz, CF); $^{19}F$ NMR (282 MHz, $CD_3OD$, δ): −121.5 to −121.4 (m, CF); TLC: $R_f$=0.22 (40:1 dichloromethane/methanol); HRESIMS (m/z): $[M+H]^+$ calcd for $C_{10}H_{14}O_4F$, 217.0876. found, 217.0874.

2,2'-(4-Fluoro-1,2-phenylene)bisoxybis(ethane-2,1-diyl) bis(4-methylbenzenesulfonate) (9): To a mixture of diol 8 (0.501 g, 2.30 mmol, 1 equiv) and triethylamine (3 mL) at 0° C. under an atmosphere of Ar was added a solution of 4-methylbenzene-1-sulfonyl chloride (1.32 g, 6.90 mmol, 3 equiv) in dichloromethane (9 mL) dropwise over 30 minutes. Upon completion of the addition, the mixture was warmed to ambient temperature and stirred for 24 hours. The resulting solution was washed sequentially with water (3×25 mL), saturated aqueous $NaHCO_3$ (3×25 mL), and saturated aqueous citric acid (3×25 mL). The organic layer was dried over anhydrous $Na_2SO_4$, and the solvent was removed under reduced pressure. Purification was performed using silica gel chromatography (stepwise gradient of 1:0→3:1→1:1 hexanes/ethyl acetate) to yield 0.930 g (77%) of the product as a pale yellow solid. $^1H$ NMR (300 MHz, $CDCl_3$, δ): 2.44

(s, CH$_3$, 6H), 4.08-4.18 (m, CH$_2$, 4H), 4.25-4.37 (m, CH$_2$, 4H), 6.47-6.62 (m, CH, 2H), 6.72-6.81 (m, CH, 1H), 7.34 (d, J=7.8 Hz, CH, 4H), 7.80 (d, J=7.8 Hz, CH, 4H); $^{13}$C NMR (75 MHz, CDCl$_3$, δ): 21.8 (CH$_3$), 67.4 (CH$_2$), 68.1 (CH$_2$), 68.5 (CH$_2$), 68.6 (CH$_2$), 103.7 (d, $^2J_{C-F}$=26.2 Hz, CH), 108.1 (d, $^2J_{C-F}$=22.2 Hz, CH), 118.2 (d, $^3J_{C-F}$=9.0 Hz, CH), 128.1 (CH), 130.1 (CH), 132.9, 144.6, 145.2, 149.7 (d, $^3$JC-F=10.0 Hz), 158.3 (d, $^1J_{C-F}$=241.7 Hz, CF); $^{19}$F NMR (282 MHz, CDCl$_3$, δ): −118.5 to −118.4 (m, CF); TLC: R$_f$=0.27 (3:1 hexanes/ethyl acetate); HRESIMS (m/z): [M+Na]$^+$ calcd for C$_{24}$H$_{25}$O$_8$FS$_2$Na, 547.0873. found, 547.0872.

5,6-(4-Fluorobenzo)-4,7,13,16,21,24-hexaoxa-1,10-diazabicyclo[8.8.8]hexacos-5-ene (4): To a mixture of 1,4,10,13-tetraoxa-7,16-diazacyclooctadecane (0.052 g, 0.20 mmol, 1 equiv) and anhydrous Cs$_2$CO$_3$ (0.652 g, 2.00 mmol, 10 equiv) under an atmosphere of Ar was added anhydrous acetonitrile (10 mL) followed by ditosylate 9 (0.115 g, 0.220 mmol, 1.1 equiv). The reaction mixture was heated at reflux for 168 hours, cooled to ambient temperature, and filtered through Whatman number 1 filter paper. The solvent was removed under reduced pressure, and purification of the resulting residue was performed using silica gel chromatography (stepwise gradient of 50:1→10:1→5:1 methanol/ammonium hydroxide (28-30% aqueous solution)) to obtain a pale yellow oil that was further purified using silica gel chromatography (9:1 dichloromethane/methanol). The resulting product was dissolved in dichloromethane and filtered through Whatman number 1 filter paper. The solvent was removed under reduced pressure to yield 10 mg (11%) of 4 as a colorless oil. $^1$H NMR (400 MHz, CD$_3$OD, δ): 2.60-2.89 (m, CH$_2$, 12H), 3.38-3.70 (m, CH$_2$, 16H), 4.14-4.24 (m, CH$_2$, 4H), 6.63-6.75 (m, CH, 1H), 6.92 (d, J=10.4 Hz, CH, 1H), 6.97-7.08 (m, CH, 1H); $^{13}$C NMR (101 MHz, CD$_3$OD, δ): 53.8 (CH$_2$), 53.9 (CH$_2$), 54.3 (CH$_2$), 66.7 (CH$_2$), 66.8 (CH$_2$), 68.7 (CH$_2$), 68.8 (CH$_2$), 69.29 (CH$_2$), 69.34 (CH$_2$), 102.3 (d, $^2J_{C-F}$=27.7 Hz, CH), 107.4 (d, $^2J_{C-F}$=23.1 Hz, CH), 114.0 (d, $^3J_{C-F}$=10.5 Hz, CH); $^{19}$F NMR (282 MHz, CDCl$_3$, δ): −120.3 to −120.1 (m, CF); TLC: R$_f$=0.26 (5:1 methanol/ammonium hydroxide (20-30% aqueous solution)); HRESIMS (m/z): [M+H]$^+$ calcd for O$_{22}$H$_{36}$N$_2$O$_6$F, 443.2557. found, 443.2557.

2,2'-(1,2-Phenylenebisoxy)diethanol (10): To a degassed solution of water (1 mL), 1-butanol (2.5 mL), and NaOH (0.545 g, 13.6 mmol, 3 equiv) under an atmosphere of Ar was added catechol (0.500 g, 4.54 mmol, 1 equiv), and the resulting mixture was heated at reflux. After 5 minutes at reflux, a degassed solution of 2-chloroethanol (912 µL, 13.6 mmol, 3 equiv) in 1-butanol (12.5 mL) was added dropwise over 1 hour while maintaining reflux. The resulting solution was heated at reflux for 18 hours at which point the solvent was removed under reduced pressure. Purification was performed using silica gel chromatography (stepwise gradient of 1:1→1:3→0:1 hexanes/ethyl acetate) to yield 546 mg (61%) of 10 as a white solid. $^1$H NMR (300 MHz, CD$_3$OD, δ): 3.87 (t, J=4.6 Hz, CH$_2$, 4H), 4.07 (t, J=4.6 Hz, CH$_2$, 4H), 6.86-7.05 (m, CH, 4H); $^{13}$C NMR (75 MHz, CD$_3$OD, δ): 61.7 (CH$_2$), 72.0 (CH$_2$), 115.6 (CH), 122.7 (CH), 150.3; TLC: R$_f$=0.14 (1:1 hexanes/ethyl acetate); HRESIMS (m/z): [M+Na]$^+$ calcd for C$_{10}$H$_{14}$O$_4$Na, 221.0790. found, 221.0794.

2,2'-(1,2-Phenylenebisoxy)bis(ethane-2,1-diyl)bis(4-methylbenzenesulfonate) (11): To a mixture of diol 10 (2.00 g, 10.1 mmol, 1 equiv) and triethylamine (8.5 mL) at 0° C. under an atmosphere of Ar was added a solution of 4-methylbenzene-1-sulfonyl chloride (5.771 g, 30.27 mmol, 3 equiv) in dichloromethane (27.5 mL) dropwise over 2 hours. Upon completion of the addition, the reaction mixture was warmed to ambient temperature and stirred for 24 hours. The resulting solution was washed sequentially with water (3×50 mL), saturated aqueous NaHCO$_3$ (3×50 mL), and saturated aqueous citric acid (3×50 mL). The organic layer was dried over anhydrous Na$_2$SO$_4$, and the solvent was removed under reduced pressure. Purification was performed using silica gel chromatography (stepwise gradient of 1:0→5:1→3:1→0:1 hexanes/ethyl acetate) to yield 3.72 g (73%) of 11 as a white solid. $^1$H NMR (400 MHz, CDCl$_3$, δ): 2.44 (s, CH$_3$, 6H), 4.17 (t, J=4.8 Hz, CH$_2$, 4H), 4.33 (t, J=4.8 Hz, CH$_2$, 4H), 6.79-6.85 (m, CH, 2H), 6.88-6.94 (m, CH, 2H), 7.34 (d, J=8.0 Hz, CH, 4H), 7.81 (d, J=8.8 Hz, CH, 4H); $^{13}$C NMR (75 MHz, CDCl$_3$, δ): 21.8 (CH$_3$), 67.5 (CH$_2$), 68.4 (CH$_2$), 116.5 (CH), 122.8 (CH), 128.1 (CH), 130.1 (CH), 133.1, 145.2, 148.6; TLC: R$_f$=0.20 (3:1 hexanes/ethyl acetate); HRESIMS (m/z): [M+Na]$^+$ calcd for C$_{24}$H$_{26}$O$_8$S$_2$Na, 529.0967. found, 529.0948.

5,6,14,15-Dibenzo-4,7,13,16,21,24-hexaoxa-1,10-diazabicyclo[8.8.8]hexacosane (5): To a mixture of Cs$_2$CO$_3$ (1.96 g, 6.01 mmol, 6 equiv) in acetonitrile (100 mL) at reflux was added a solution of ditosylate 11 (1.04 g, 2.05 mmol, 2.05 equiv) and 2,2'-(ethylenedioxy)bis(ethylamine) (146 µL, 1.00 mmol, 1 equiv) in acetonitrile (100 mL) dropwise over 48 hours. Upon complete addition, the resulting mixture was heated at reflux for 120 hours. Solvent was removed under reduced pressure, and purification was performed using silica gel chromatography (stepwise gradient of 1:0→50:1→8:1 dichloromethane/methanol) to obtain a light yellow oil that was further purified using silica gel chromatography (stepwise gradient of 20:1→5:1 methanol/ammonium hydroxide (28-30% aqueous solution)). After removing solvent under reduced pressure, the resulting product was dissolved in dichloromethane and was filtered through glass wool. The solvent was removed under reduced pressure to yield 61 mg (13%) of 5 as a light yellow oil. $^1$H NMR (400 MHz, CDCl$_3$, δ): 2.87 (t, J=5.6 Hz, CH$_2$, 4H), 3.02-3.20 (m, CH$_2$, 8H), 3.49 (s, CH$_2$, 4H), 3.56 (t, J=5.2 Hz, CH$_2$, 4H), 4.13 (t, J=6.2 Hz, CH$_2$, 8H), 6.88 (d, J=2.4 Hz, CH, 8H); $^{13}$C NMR (75 MHz, CDCl$_3$, δ): 55.2 (CH$_2$), 68.3 (CH$_2$), 70.6 (CH$_2$), 70.9 (CH$_2$), 77.4 (CH$_2$), 115.2 (CH), 121.6 (CH) 149.4; TLC: R$_f$=0.46 (8:1 dichloromethane/methanol); HRESIMS (m/z): [M+Na]$^+$ calcd for C$_{26}$H$_{36}$N$_2$O$_6$Na, 495.2471. found, 495.2473.

5,6-Benzo-4,7-dioxa-13,16,21,24-tetrathia-1,10-diazabicyclo[8.8.8]hexacos-5-ene (6): To a mixture of 1,4,10,13-tetrathia-7,16-diazacyclooctadecane (0.053 g, 0.16 mmol, 1 equiv) and anhydrous Cs$_2$CO$_3$ (0.525 g, 1.61 mmol, 10 equiv) under an atmosphere of Ar was added anhydrous acetonitrile (10 mL) followed by ditosylate 11 (0.086 g, 0.17 mmol, 1.05 equiv). The reaction mixture was heated at reflux for 120 hours, cooled to ambient temperature, and filtered through Whatman number 1 filter paper. The solvent was removed under reduced pressure, and purification of the resulting residue was performed using silica gel chromatography (stepwise gradient of 1:0→30:1→20:1→10:1→5:1 dichloromethane/methanol). The resulting product was further purified using silica gel chromatography (stepwise gradient of 1:0→4:1→1:1→0:1 hexane/ethyl acetate). The solvent was removed under reduced pressure to yield 10 mg (13%) of 6 as a white solid. $^1$H NMR (300 MHz, CDCl$_3$, δ): 2.58-3.05 (m, CH$_2$, 24H), 4.20 (t, J=5.0 Hz, CH$_2$, 4H), 6.92 (brs, CH, 4H); $^{13}$C NMR (75 MHz, CDCl$_3$, δ): 30.6 (CH$_2$), 32.8 (CH$_2$), 54.8 (CH$_2$), 57.2 (CH$_2$), 68.2 (CH$_2$), 114.9 (CH), 121.7 (CH), 149.0; TLC: R$_f$=0.33 (30:1 dichloromethane/methanol), 0.22 (4:1 hexane/ethyl acetate); HRESIMS (m/z): [M+Na]$^+$ calcd for $C_{22}H_{36}N_2O_2S_4Na$, 511.1557. found, 511.1552.

Eu$^{II}$ Cryptate Formation

To an aqueous solution of 3-(N-morpholino)propanesulfonic acid (MOPS) (0.01 M, pH 7.5), Et$_4$NClO$_4$ (0.05 M), and Eu(NO$_3$)$_3$.5H$_2$O (1.1 mM, 1 equiv) was added a solution of the desired cryptand (12 mM, 1.2 equiv) in acetonitrile, and the resulting mixture was sparged with Ar for 5 minutes. The potential of the resulting solution was held at −0.8 V (30 minutes per 0.01 mmol of Eu(NO$_3$)$_3$.5H$_2$O) while stirring under constant sparging with Ar. Immediately after holding the potential at −0.8 V, cyclic voltammograms were obtained in the potential range of −1.5 to 0.75 V at a scan rate of 150 mV/s. After acquiring the voltammogram, ferrocene (6.7 mM in acetonitrile, 0.1 equiv) was added, and another cyclic voltammogram was obtained. These cyclic voltammetric experiments were repeated 3-6 times for each ligand. Cyclic voltammograms of ligands 1-6 were obtained using the same protocol without Eu.

Throughout this application various publications, including United States patents are referenced, author and year and patents by number reference. Full citations for the publications are listed below. The disclosures of these publications and patents in their entireties are hereby incorporated by reference into this application in order to more fully describe the state of the art to which this invention pertains.

The invention has been described in an illustrative manner, and it is to be understood that the terminology, which has been used herein, is intended to be in the nature of words of description rather than of limitation.

Obviously, many modifications and variations of the present invention are possible in light of the above teachings. It is, therefore, to be understood that within the scope of the described invention, the invention can be practiced otherwise than as specifically described.

REFERENCES

F. Stadler, O. Oeckler, H. A. Höppe, M. H. Möller, R. Pöttgen, B. D. Mosel, P. Schmidt, V. Duppel, A. Simon, W. Schnick, Chem. Eur. J. 2006, 12, 6984-6990.

G. Denis, P. Deniard, E. Gautron, F. Clabau, A. Garcia, S. Jobic, Inorg. Chem. 2008, 47, 4226-4235.

V. M. Huxter, T. Mirkovic, P. S. Nair, G. D. Scholes, Adv. Mater. 2008, 20, 2439-2443.

W. J. Evans, J. M. Perotti, J. C. Brady, J. W. Ziller, J. Am. Chem. Soc. 2003, 125, 5204-5212.

S. Datta, M. T. Gamer, P. W. Roesky, Organometallics 2008, 27, 1207-1213.

F. T. Edelmann, Chem. Soc. Rev. 2009, 38, 2253-2268.

M. M. Richter, A. J. Bard, Anal. Chem. 1996, 68, 2641-2650.

F. H. Su, W. Chen, K. Ding, G. H. Li, J. Phys. Chem. A 2008, 112, 4772-4777.

V. Petrykin, M. Kakihana, Chem. Mater. 2008, 20, 5128-5130.

K. Ahn, A. O. Pecharsky, K. A. Gschneidner, V. K. Pecharsky, J. Appl. Phys. 2004, 97, 1-5.

Y. Hasegawa, T. Adachi, A. Tanaka, M. Afzaal, P. O'Brien, T. Doi, Y. Hinatsu, K. Fujita, K. Tanaka, T. Kawai, J. Am. Chem. Soc. 2008, 130, 5710-5715.

M. D. Regulacio, S. Kar, E. Zuniga, G. Wang, N. R. Dollahon, G. T. Yee, S. L. Stoll, Chem. Mater. 2008, 20, 3368-3376.

É. Tóth, L. Burai, A. E. Merbach, Coord. Chem. Rev. 2001, 216-217, 363-382.

S. Viswanathan, Z. Kovacs, K. N. Green, S. J. Ratnakar, A. D. Sherry, Chem. Rev. 2010, 110, 2960-3018.

E. L. Yee, O. A. Gansow, M. J. Weaver, J. Am. Chem. Soc. 1980, 102, 2278-2285;

L. Burai, É. Tóth, G. Moreau, A. Sour, R. Scopelliti, Chem. Eur. J. 2003, 9, 1394-1404.

O. A. Gansow, A. R. Kausar, K. M. Triplett, M. J. Weaver, E. L. Yee, J. Am. Chem. Soc. 1977, 99, 7087-7089.

L. Burai, R. Scopelliti, É. Tóth, Chem. Commun. 2002, 2366-2367.

N. Sabbatini, M. Ciano, S. Dellonte, A. Bonazzi, F. Bolletta, V. Balzani, J. Phys. Chem. 1984, 88, 1534-1537.

J.-L. Yuan, X.-Y. Zeng, J.-T. Zhao, Z.-J. Zhang, H.-H. Chen, G.-B. Zhang, J. Solid State Chem. 2007, 180, 3310-3316.

W. J. Evans, M. A. Johnston, M. A. Greci, J. W. Ziller, Organometallics 1999, 18, 1460-1464.

S. Hauber, M. Niemeyer, Inorg. Chem. 2005, 44, 8644-8646.

H. Guo, H. Zhou, Y. Yao, Y. Zhang, Q. Shen, Dalton. Trans. 2007, 3555-3561.

R. Puchta, R. Meier, R. V. Eldik, Aust. J. Chem. 2007, 60, 889-897.

D. T. Dugah, B. W. Skelton, E. E. Delbridge, Dalton Trans. 2009, 1436-1445.

B. G. Cox, N. V. Truong, J. Garcia-Rosas, H. Schneider, J. Phys. Chem. 1984, 88, 996-1001.

D. A. Dantz, H.-J. Buschmann, E. Schollmeyer, Polyhedron 1998, 17, 1891-1895.

J. M. Bemtgen, M. E. Springer, V. M. Loyola, R. G. Wilkins, R. W. Taylor, Inorg. Chem. 1984, 23, 3348-3353.

R. Gagne, C. Koval, G. Licenski, Inorg. Chem. 1980, 19, 2854-2855.

Denmark, S. E.; Heemstra, J. R., Jr.; Beutner, G. L. Angew. Chem. Int. Ed. 2005, 44, 4682-4698.

Schetter, B.; Mahrwald, R. Angew. Chem. Int. Ed. 2006, 45, 7506-7525.

Fukui, H.; Shiina, I. Org. Lett. 2008, 10, 3153-3156.

Chakraborty, T. K.; Chattopadhyay, A. K. J. Org. Chem. 2008, 73, 3578-3581.

Sabitha, G.; Gopal, P.; Reddy, C. N.; Yadav, J. S. Synthesis 2009, 3301-3304.

Wang, L.; Gong, J.; Deng, L.; Xiang, Z.; Chen, Z.; Wang, Y.; Chen, J.; Yang, Z. Org. Lett. 2009, 11, 1809-1812.

Kobayashi, S.; Hachiya, I. J. Org. Chem. 1994, 59, 3590-3596.

Kobayashi, S.; Hamada, T.; Nagayama, S.; Manabe, K. Org. Lett. 2001, 3, 165-167.

Hamada, T.; Manabe, K.; Ishikawa, S.; Nagayama, S.; Shiro, M.; Kobayashi, S. J. Am. Chem. Soc. 2003, 125, 2989-2996.

Dissanayake, P.; Allen, M. J. J. Am. Chem. Soc. 2009, 131, 6342-6343.

Caravan, P.; Ellison, J. J.; McMurry, T. J.; Lauffer, R. B. Chem. Rev. 1999, 99, 2293-2352.

Kobayashi, S.; Hachiya, I. Tetrahedron Lett. 1992, 33, 1625-1628.

Horrocks, W. D., Jr.; Sudnick, D. R. J. Am. Chem. Soc. 1979, 101, 334-340.

Corey, E. J.; Rhode, J. J.; Fischer, A.; Azimioara, M. D. Tetrahedron Lett. 1997, 38, 33-36. (b) Ishihara, K.; Kondo, S.; Yamamoto, H. J. Org. Chem. 2000, 65, 9125-9128. (c) Corey, E. J.; Lee, T. W. Chem. Commun. 2001, 1321-1329.

D. R. Alston, J. F. Stoddart, J. B. Wolstenholme, B. L. Allwood, D. J. Williams, Tetrahedron 1985, 41, 2923-2926.

C. W. Still, M. Kahn, A. Mitra, J. Org. Chem. 1978, 43, 2923-2925.

R. Gagne, C. Koval, G. Licenski, Inorg. Chem. 1980, 19, 2854-2855.

O. A. Gansow, A. R. Kausar, K. M. Triplett, M. J. Weaver, E. L. Yee, J. Am. Chem. Soc. 1977, 99, 7087-7089.

What is claimed is:

1. An oxidatively-stable Eu(II) complex comprising:
an Eu(II) ion; and
a ligand having a formula selected from the group consisting of:

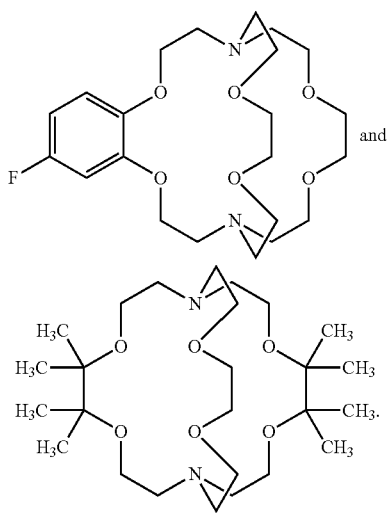

and

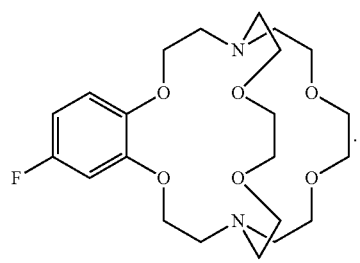 [SMILES: Fc1ccc2c(c1)OCCN1CCOCCOCCN(CCOCCOCC1)CCO2]

2. The Eu(II) complex of claim 1 wherein the ligand has formula:

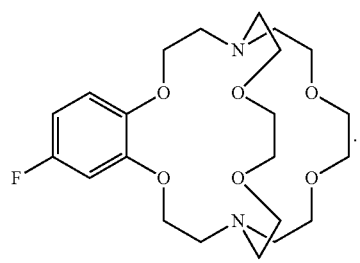 [SMILES: Fc1ccc2c(c1)OCCN1CCOCCOCCN(CCOCCOCC1)CCO2]

3. The Eu(II) complex of claim 1 wherein the ligand has formula:

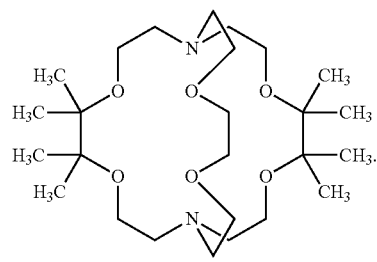 [SMILES: CC1(C)OCCN2CCOCCOCCN(CCOC1(C)C)CCOC(C)(C)C(C)(C)OCC2]

4. The Eu(II) complex according to claim 1, further comprising a compound selected from the group consisting of proteins, dendrimers, biomolecules, and polymers, bound to the Eu(II) complex.

5. The Eu(II) complex according to claim 1 for use as a contrast agent in magnetic resonance imaging.

6. The Eu(II) complex according to claim 1 for use as a contrast agent in ultra-high field magnetic resonance imaging.

7. The Eu(II) complex according to claim 6, wherein said magnetic resonance imaging uses an ultra-high field that is greater than 3 Tesla.

8. The Eu(II) complex according to claim 1 for use in diagnostic medical applications.

9. An oxidatively-stable Eu(II) complex comprising:
an Eu(II) ion; and
a ligand having a formula selected from the group consisting of:

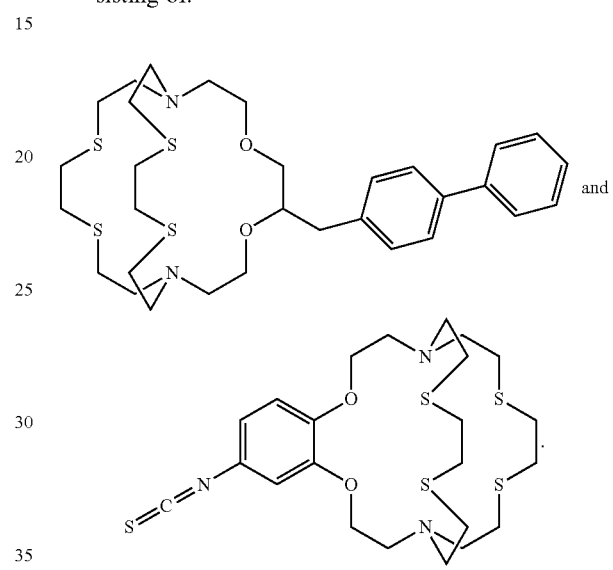

and

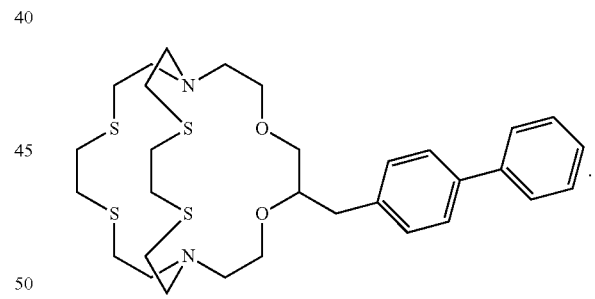

10. The Eu(II) complex of claim 9 wherein the ligand has formula:

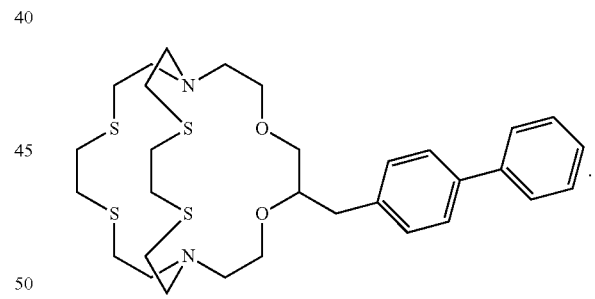

11. The Eu(II) complex of claim 9 wherein the ligand has formula:

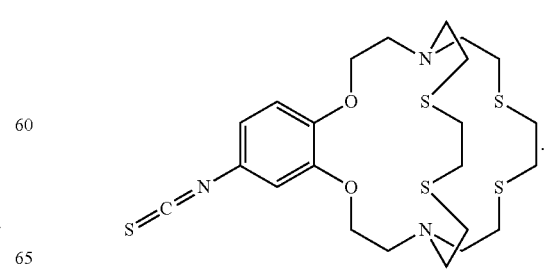

12. The Eu(II) complex according to claim 9, further comprising a compound selected from the group consisting of proteins, dendrimers, biomolecules, and polymers, bound to the Eu(II) complex.

13. The Eu(II) complex according to claim 9 for use as a contrast agent in magnetic resonance imaging.

14. The Eu(II) complex according to claim 9 for use as a contrast agent in ultra-high field magnetic resonance imaging.

15. The Eu(II) complex according to claim 14, wherein said magnetic resonance imaging uses an ultra-high field that is greater than 3 Tesla.

16. The Eu(II) complex according to claim 9 for use in diagnostic medical applications.

* * * * *